US012629256B2

(12) United States Patent
Hay

(10) Patent No.: US 12,629,256 B2
(45) Date of Patent: *May 19, 2026

(54) SYSTEMS AND METHODS FOR MANUFACTURING ORTHOPEDIC PROSTHESES

(71) Applicant: James Scott Hay, Parkland, FL (US)

(72) Inventor: James Scott Hay, Parkland, FL (US)

( * ) Notice: Subject to any disclaimer, the term of this patent is extended or adjusted under 35 U.S.C. 154(b) by 1146 days.

This patent is subject to a terminal disclaimer.

(21) Appl. No.: 17/588,465

(22) Filed: Jan. 31, 2022

(65) Prior Publication Data

US 2022/0151790 A1 May 19, 2022

Related U.S. Application Data

(63) Continuation-in-part of application No. 16/990,490, filed on Aug. 11, 2020, now Pat. No. 11,266,504.

(51) Int. Cl.
*A61F 2/30* (2006.01)
*A61F 2/38* (2006.01)

(52) U.S. Cl.
CPC ...... *A61F 2/30942* (2013.01); *A61F 2/30734* (2013.01); *A61F 2/3859* (2013.01); *A61F 2/389* (2013.01)

(58) Field of Classification Search
CPC .... A61F 2/3859; A61F 2/30942; A61F 2/389; A61F 2/3662; A61F 2/30734; A61F 2/3609; A61F 2002/30672; A61F 2002/30677; A61F 2002/365; A61F 2002/30957
See application file for complete search history.

(56) References Cited

U.S. PATENT DOCUMENTS

| | | | |
|---|---|---|---|
| 3,907,245 A | 9/1975 | Linder | |
| 3,990,672 A | 11/1976 | Buchanan | |
| 5,123,927 A | 6/1992 | Duncan et al. | |
| 5,236,457 A | 8/1993 | Devanathan | |
| 5,535,810 A * | 7/1996 | Compton | ........... A61F 2/30767 |
| | | | 164/35 |
| 5,538,514 A | 7/1996 | Hawkins | |
| 6,040,354 A * | 3/2000 | Hubner | .................. A61K 6/90 |
| | | | 264/16 |
| 6,155,812 A | 12/2000 | Smith | |
| 6,361,731 B1 | 3/2002 | Smith | |
| 6,942,475 B2 | 9/2005 | Ensign | |

(Continued)

*Primary Examiner* — Christina A Johnson
*Assistant Examiner* — Kelsey C Grace
(74) *Attorney, Agent, or Firm* — Mark Terry

(57) ABSTRACT

An orthopedic prosthesis mold, comprising a first housing including a first cavity therein shaped to form a portion of an orthopedic prosthesis; a second housing coupled to the first housing, the second housing including a second cavity therein shaped to form a portion of an orthopedic prosthesis, wherein the first and second housings are constructed from a material having a first hardness; a first shell element configured to receive at least a portion of the first housing therein; a second shell element configured to receive at least a portion of the first housing therein, wherein the first and second shell elements are constructed from a material having a second hardness greater than the first hardness; and a connection element releasably engageable to the first and second shell elements to prevent separation of the first shell element from the second shell element.

18 Claims, 19 Drawing Sheets

(56) References Cited

U.S. PATENT DOCUMENTS

| | | | | |
|---|---|---|---|---|
| 7,427,296 | B2 | 9/2008 | Evans | |
| 7,429,346 | B2 | 9/2008 | Ensign | |
| 7,789,646 | B2 | 9/2010 | Haney | |
| 9,056,011 | B2 * | 6/2015 | Stolarski | A61F 2/30942 |
| 11,266,504 | B1 * | 3/2022 | Hay | A61F 2/3609 |
| 2007/0222114 | A1 | 9/2007 | Ziran | |
| 2010/0102484 | A1 | 4/2010 | Haney | |
| 2018/0280144 | A1 * | 10/2018 | Jones | B33Y 50/00 |

* cited by examiner 124
104
136b 202
232
228
200
240
204

242

244

343

302

342

442

SYSTEMS AND METHODS FOR MANUFACTURING ORTHOPEDIC PROSTHESES

CROSS-REFERENCE TO RELATED APPLICATION

This application is a continuation-in-part-of patent application Ser. No. 16/990,490, filed Aug. 11, 2020, entitled SYSTEMS AND METHODS FOR MANUFACTURING ORTHOPEDIC PROSTHESES, the entirety of which is incorporated herein by reference.

STATEMENT REGARDING FEDERALLY SPONSORED RESEARCH OR DEVELOPMENT

N/A

FIELD OF THE INVENTION

The present disclosure relates to orthopedic prostheses and methods and systems for the manufacture thereof.

BACKGROUND OF THE INVENTION

A healthy knee joint is able to withstand great forces that are exerted as the knee flexes and extends and supports the weight of the body. However, when the knee joint becomes diseased, damaged or is otherwise unable to withstand the forces required of that joint, it may become necessary to reconstruct or replace the knee joint. When replacement is necessary, the natural knee joint is replaced with a prosthetic knee joint. A typical knee joint prosthesis includes a femoral component and a tibial component. During a replacement knee surgery, portions of both the tibia and femur are typically resected to allow the placement of prosthetic tibial and femoral components, which are anchored to the respective bones.

Sometimes, a small percentage of patients who undergo a total knee replacement surgery suffer from infections in the knee joint at the surgical site. To alleviate the effects of the infection, a two-stage revision of the failed knee replacement is employed. First, the failed prosthesis must be surgically removed and the site debrided and cleansed extensively in order to rid the site of the infection. Before a new, permanent prosthesis can be placed in the old surgical site, the site must be free of infection. A temporary antibiotic-impregnated cement spacer may be used as part of the therapy to rid the site of infection. Disinfecting the site of infection may take between 6-8 weeks and up to 3-4 months in most circumstances. It is thus common for surgeons to replace the old prosthetic knee with a temporary implant, typically made of bone cement, during the 6-8 week period while the infection is cleared up and before the new prosthesis is surgically implanted. The second and final step requires a separate revision surgery to then replace the temporary implant with a permanent prosthetic implant.

In the past, surgeons have been left to their own devices when forming cement implants, including the use of negative molds. The process of making a negative mold consists of the surgeon creating a mold by inserting a portion of bone cement into a bowl or other mixing container and allowing the cement to nearly cure. Prior to complete curing of the bone cement, the surgeon inserts the articulating end of the femoral component into the bone cement to create a mold. Using that mold, the surgeon then applies an oil to the mold creating a barrier for separating the cement implant from the cement mold. After applying the oil, cement may be poured into the mold allowing it cure, after which the surgeon attaches the resulting bone cement implant onto the femur as a temporary replacement.

Other methods used in the past of forming temporary implants include surgeons creating the implant with their own hands or simply putting a block of cement between the tibia and the femur to act as a spacer. However, there are many problems associated with such methods and designs, namely increased surgical time due to the preparation and formation time needed for creating the implant. Particular problems associated with the block or spacer method include completely immobilizing the knee in an extended position, after surgery, for the entire 6-8 week period, which in turn leads to soft tissue damage and further complicates the revision surgery. Therefore, reproducing the knee joint using temporary implants that simulate the natural tibial and femoral components of the knee joint is much more desirable because it permits the patient to move his/her leg through a minimal range of motion. The range of motion, while limited, significantly increases the patient's comfort over the 6-8 week period allowing the patient to bend his/her knee for sitting in a chair or for riding in a car and also increases the ease of the revision surgery because the soft tissue has not been damaged to the same extent as when the knee is completely immobilized.

Attempts have been made in the prior art to provide alternatives to surgeons creating their own negative molds or even molding a temporary implant by hand, including the use of pre-made, disposable molds. Such attempts include several drawbacks, however. For example, there may be a need for many different sized molds to accommodate the differences in size from patient to patient. Existing molds are prone to overfilling and spillage, leading to wasted materials and a messy work area. Further, some molds require a surgeon cut the mold to remove it from the implant once cured. This scoring separation can be quite cumbersome to achieve, can result in small, contaminating particles or pieces of the mold or molded prosthesis being strewn about, as well as increasing the likelihood that the molded prosthesis itself is inadvertently cut or damaged in the process. Additionally, when a mold is filled with a curable material to make the prosthesis, the pressure inside the mold can cause the mold itself (and thus the resulting prosthesis) to deform.

In view of these drawbacks, it is desirable to provide orthopedic prosthesis molds and methods of use thereof that safeguard against overfilling, spillage and deformation, are easily separable to reveal the molded prosthesis, and provide an accurate, selectable range of molded prosthesis sizes.

SUMMARY OF THE INVENTION

The present disclosure advantageously provides an orthopedic prosthesis mold, comprising: a first housing including a first cavity therein shaped to form a portion of an orthopedic prosthesis; a second housing coupled to the first housing, the second housing including a second cavity therein shaped to form a portion of an orthopedic prosthesis, wherein the first and second housings are constructed from a material having a first hardness; a first shell element configured to receive at least a portion of the first housing therein; a second shell element configured to receive at least a portion of the first housing therein, wherein the first and second shell elements are constructed from a material having a second hardness greater than the first hardness; and a connection element releasably engageable to the first and second shell elements to prevent separation of the first shell element from the second shell element. The first and second housings may be constructed from a material having a hardness between Shore 40A and 80A. The first and second shell elements may be constructed from a material having a hardness between Shore 40D and 80D. The first and second housings may align with and attach to one another along a first axis, and the first and second shell elements may align with and attach to one another along a second axis that is not parallel to the first axis.

At least one of the first and second cavities may define an anterior portion and a posterior portion shaped to form a femoral knee joint prosthesis. At least one of the first and second cavities may be shaped to form a tibial knee joint prosthesis. The orthopedic prosthesis may include a plurality of spacing elements positionable within the second cavity of the second housing configured to selectively adjust a height of a prosthesis molded therein. At least one of the first and second cavities may be shaped to form a hip head prosthesis. At least one of the first and second cavities may be shaped to form a hip stem prosthesis, and may include a stem insert defining a porous lattice structure in a portion thereof.

The first housing may define an injection port. The orthopedic prosthesis mold may include an injection port cap releasably engageable with the injection port to seal the injection port. The first housing may define a plurality of vent ports.

The first housing may define a groove circumscribing the first cavity, and the second housing may define a protruding wall circumscribing the second cavity, the wall being insertable into the groove. The first and second shell elements may be substantially cylindrical. The connection element may include a threaded lock ring engaging circumferentially threaded segments of the first and second shell elements.

The first and second housings may each define one or more longitudinal grooves in exterior surfaces thereof, wherein the first and second shell elements each define one or more protruding ribs on interior surfaces thereof, and wherein the protruding ribs are positionable in the longitudinal grooves.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION OF THE INVENTION

Figure 1:
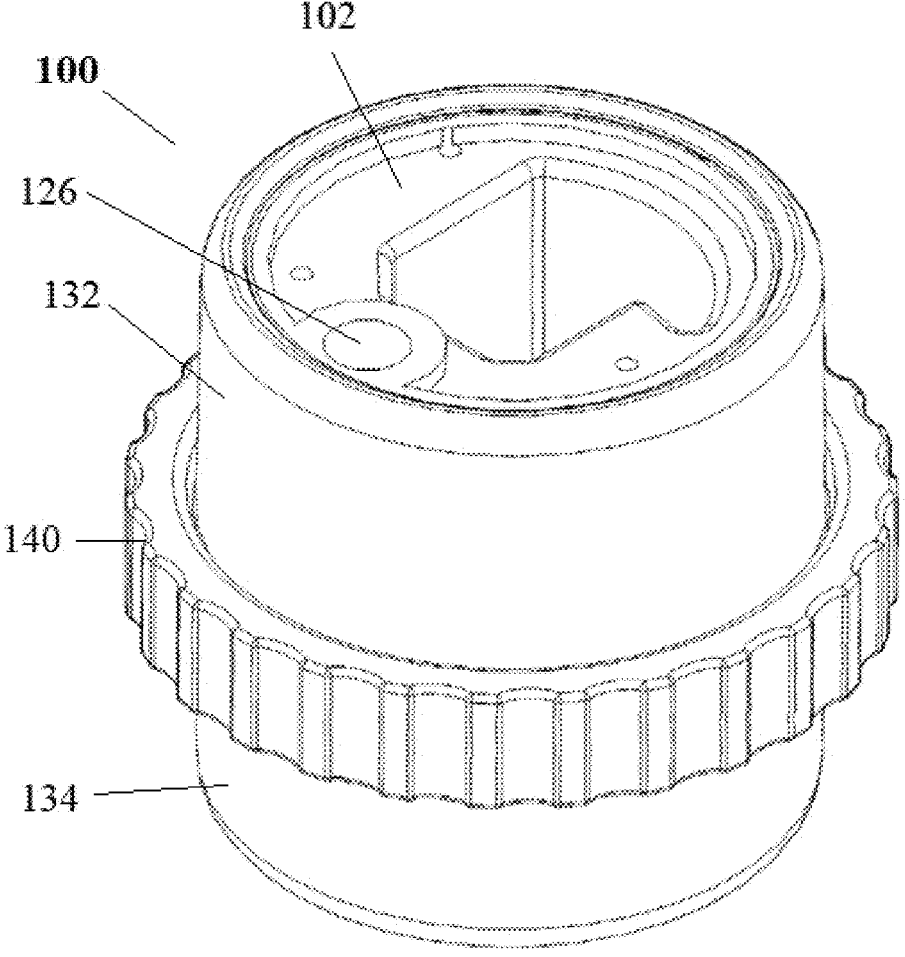
FIG. 1 is an illustration of an example of a femoral-knee orthopedic mold constructed in accordance with the present disclosure.
Figure 2:
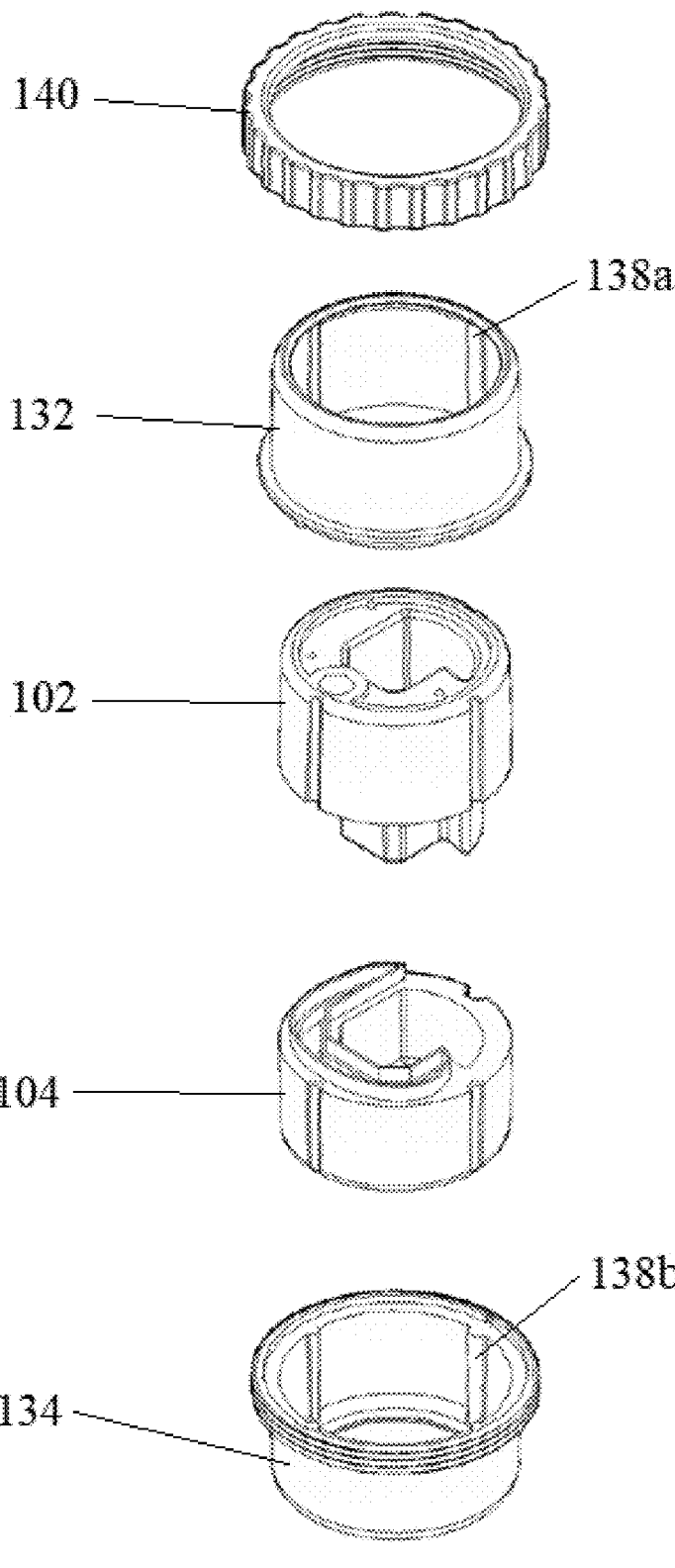
FIG. 2 is an exploded assembly illustration of the femoral-knee orthopedic mold of FIG. 1.
Figure 3:
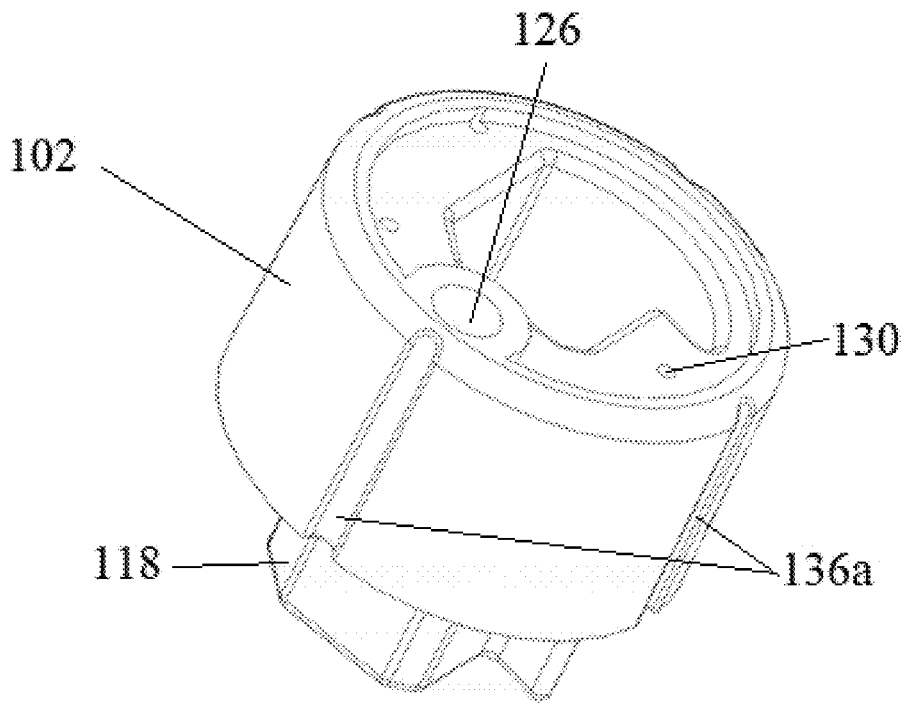
FIG. 3 is a top perspective view of an example of a first mold housing of the femoral-knee orthopedic mold of FIG. 1.

The present invention provides orthopedic prosthesis molds and methods of use thereof that safeguard against overfilling, spillage and deformation, are easily separable to reveal the molded prosthesis, and provide an accurate, selectable range of molded prosthesis sizes. The features disclosed herein provide prosthesis molds that can withstand considerable expansion forces and pressures occurring during use, which can range as high as 80 psi to 100 psi within the mold cavities. Referring now to the drawing figures in which like reference designations refer to like elements, an example of a femoral orthopedic prosthesis mold assembly constructed in accordance with principles of the present invention is shown in FIGS. 1-7 and generally designated as "100."

The mold assembly 100 generally includes a first housing or body 102 and a second housing or body 104 releasably engageable with the first housing. The first and second housings define cavities therein sized and shaped to produce an orthopedic prosthesis, such as that of a femoral and/or tibial knee joint component. For example, the first housing 102 may define or include a first cavity 106 therein for receiving a curable material to be formed or shaped into at least a portion of an orthopedic prosthesis. The second housing 104 may include a second cavity 108 for receiving a curable material to be formed or shaped into at least a portion of an orthopedic prosthesis. The second cavity 108 may be positional adjacent to and/or substantially congruous with the first cavity 106 when the first and second housings are engaged or coupled to one another to cooperatively from a substantially continuous prosthesis.

In the illustrated example, the first and second cavities 106, 108 of the first and second housings 102, 104 of the assembly 100 may be used to manufacture a femoral prosthesis for a knee joint. To form such a prosthesis, the first and second cavities 106, 108 each include an anterior portion 110 and a posterior portion 112 sized and shaped to form the resulting features of the prosthesis. The first and second housings 102, 104 of the assembly 100 shown in FIGS. 1-7 is illustrated as a femoral prosthesis mold, but it is also contemplated that the features described herein may be provided for a mold sized and shaped to form a tibial component of a knee joint, or other orthopedic prostheses.

Figure 4:
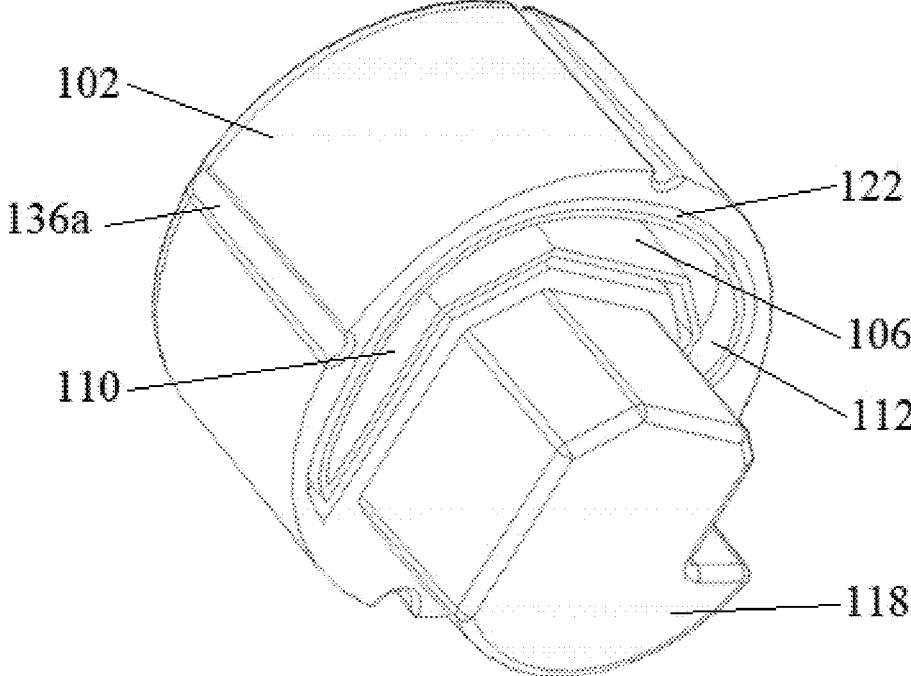
FIG. 4 is a bottom perspective view of the first mold housing of FIG. 3.
Figure 5:
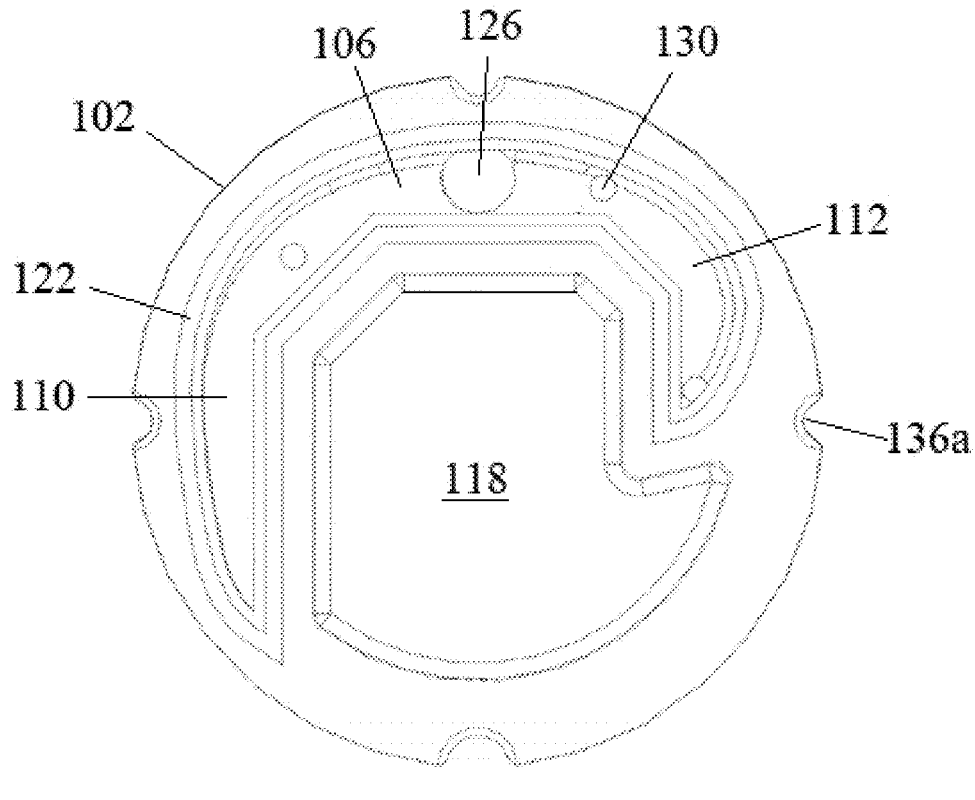
FIG. 5 is a top view of an example of a second mold housing of the femoral-knee orthopedic mold of FIG. 1.
Figure 6:
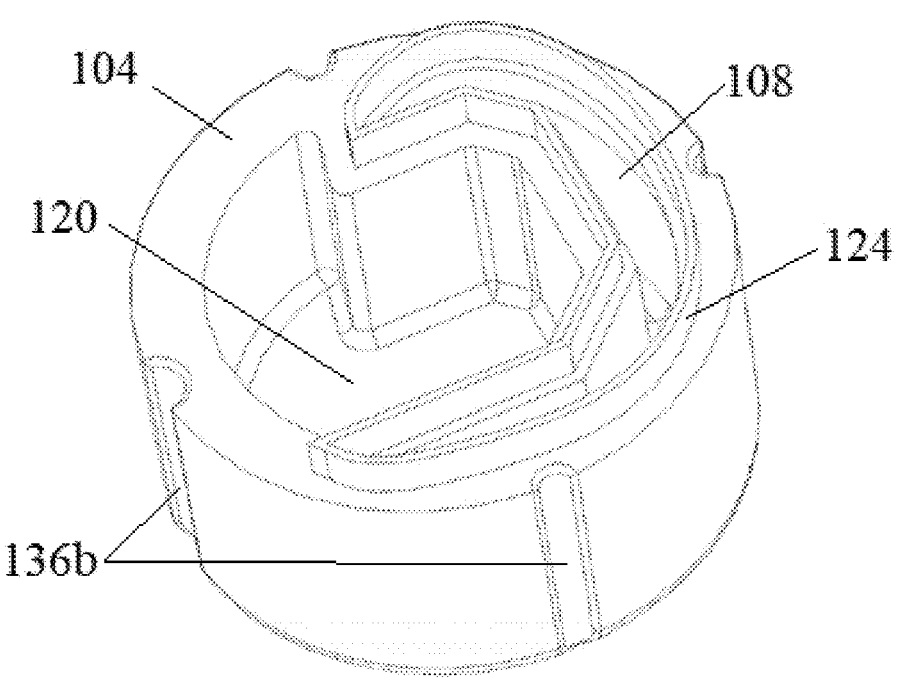
FIG. 6 is a top perspective view of the second mold housing of FIG. 5.
Figure 7:
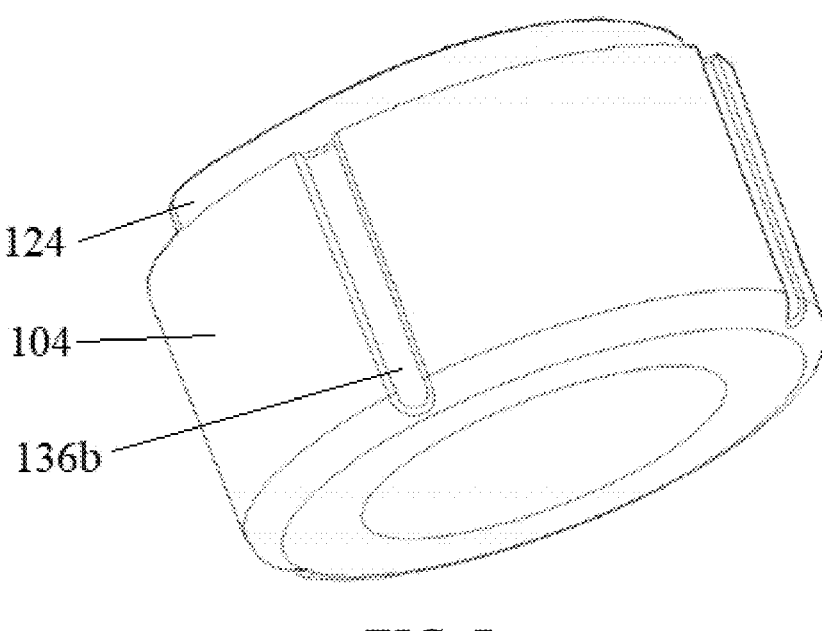
FIG. 7 is a bottom perspective view of the second mold housing of FIG. 5.
Figure 8:
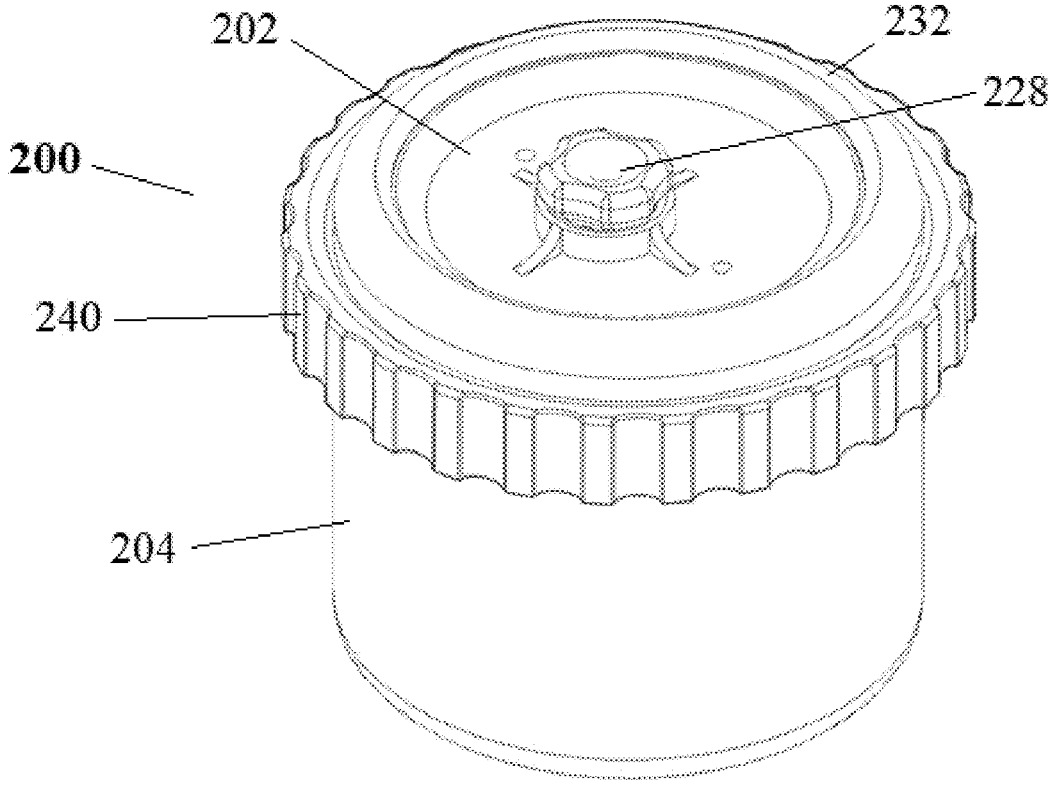
FIG. 8 is an illustration of an example of a tibial-knee orthopedic mold constructed in accordance with the present disclosure.
Figure 9:
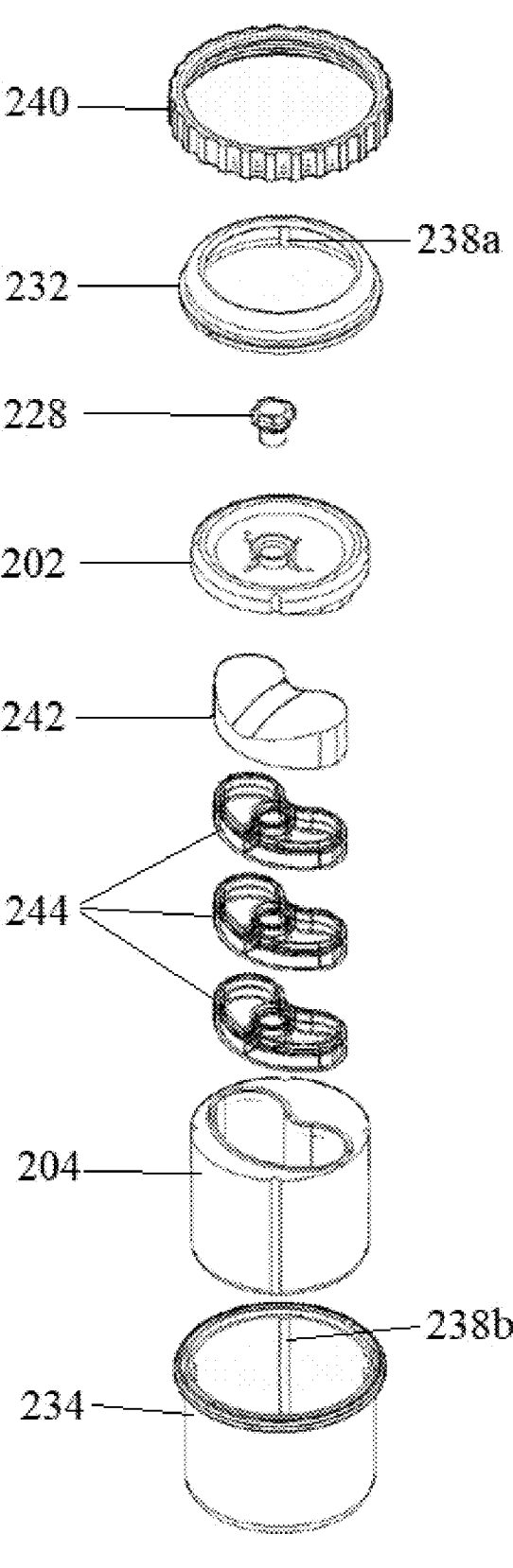
FIG. 9 is an exploded assembly illustration of the tibial-knee orthopedic mold of FIG. 8.
Figure 10:
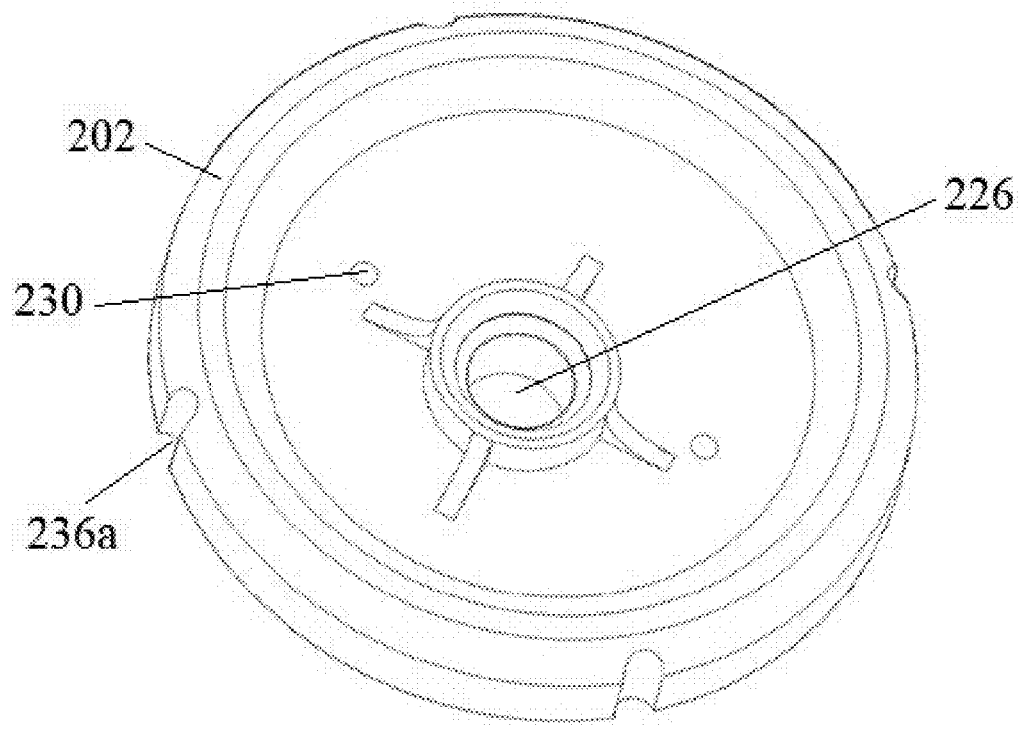
FIG. 10 is a top perspective view of an example of a first mold housing of the tibial-knee orthopedic mold of FIG. 8.
Figure 11:
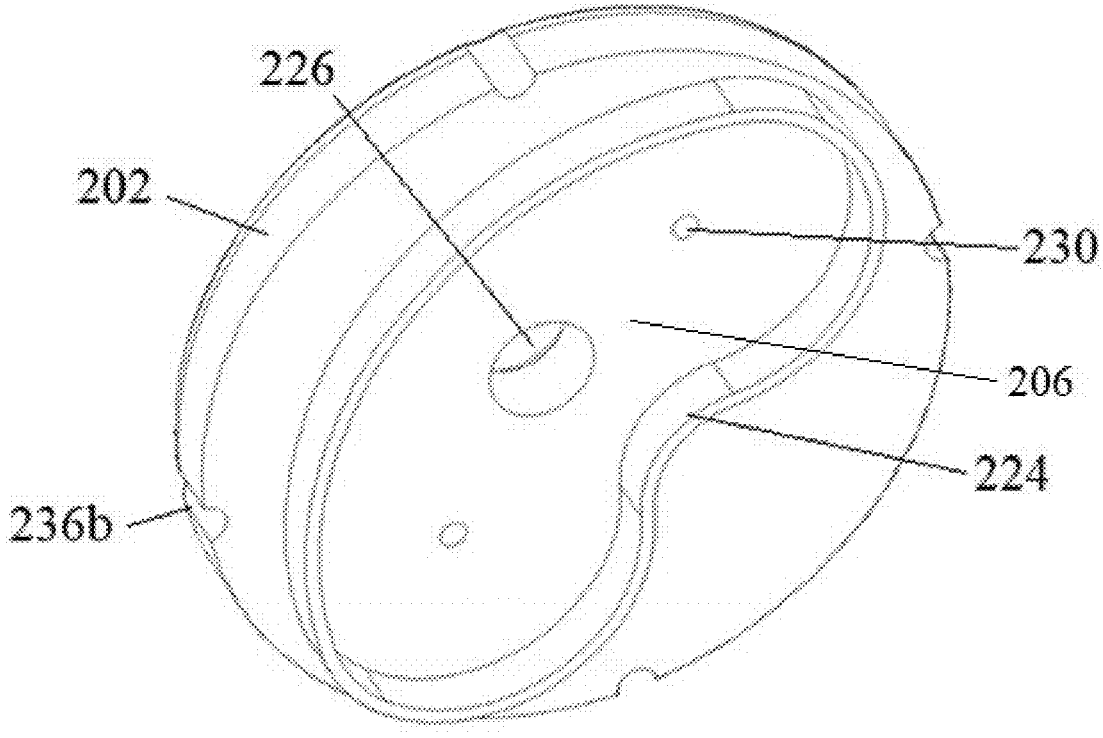
FIG. 11 is a bottom perspective view of the first mold housing of FIG. 10.
Figure 12:
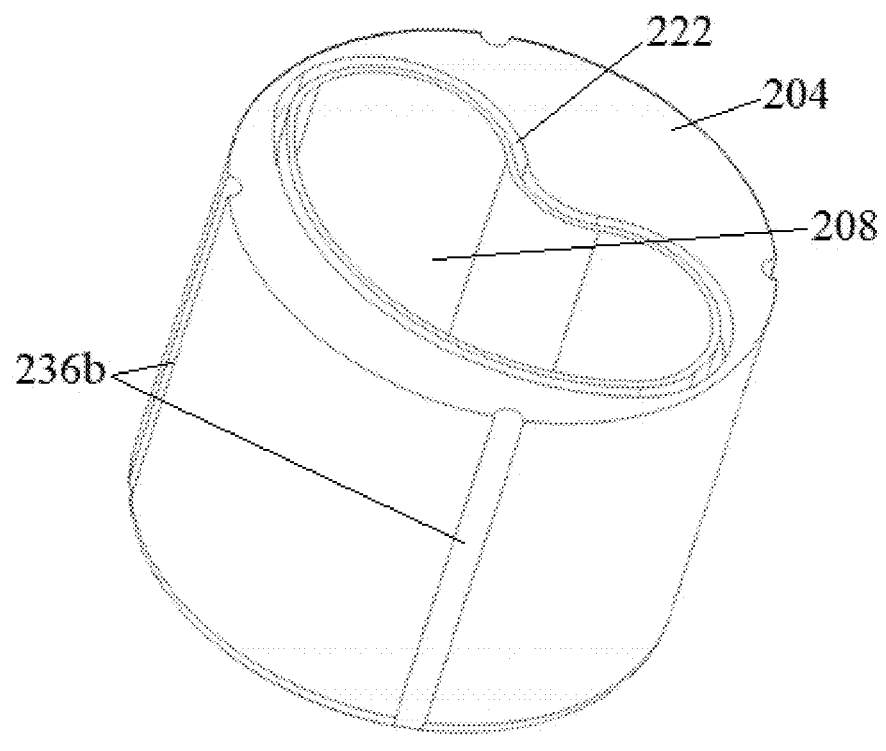
FIG. 12 is a top view of an example of a second mold housing of the tibial-knee orthopedic mold of FIG. 8.
Figure 13:
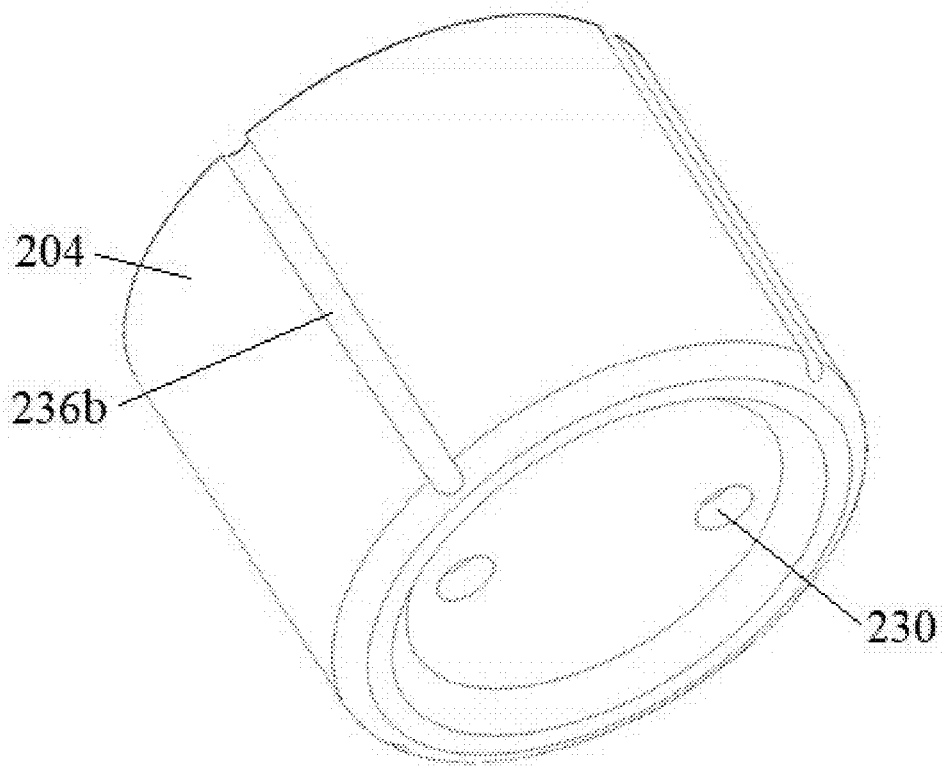
FIG. 13 is a bottom perspective view of the second mold housing of FIG. 12.
Figure 14:
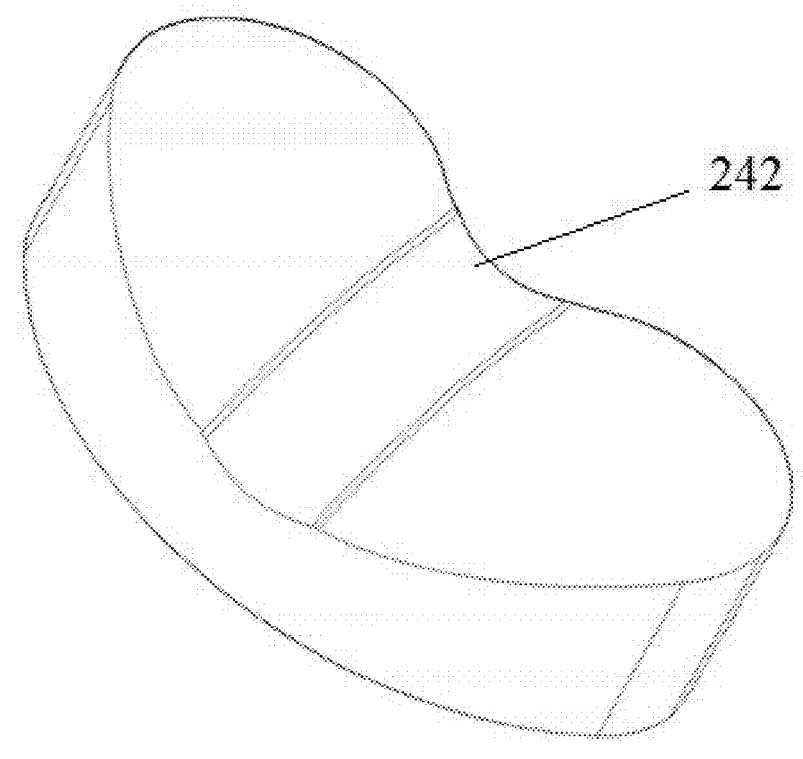
FIG. 14 is an illustration of an example of a prosthesis mold insert constructed in accordance with the present disclosure.
Figure 15:
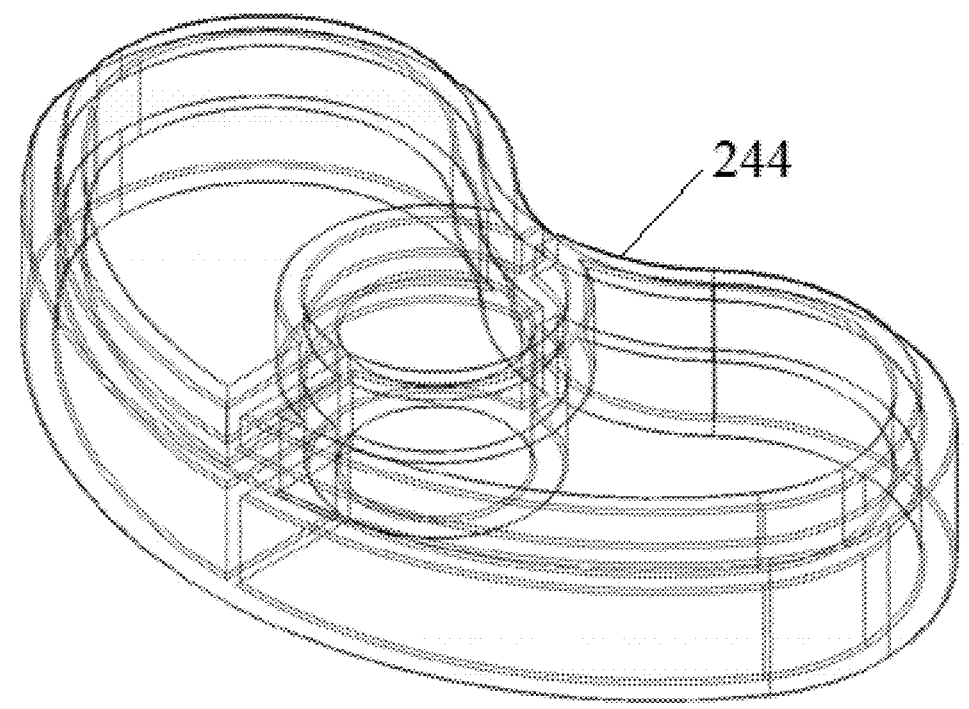
FIG. 15 is an illustration of an example of a spacing element constructed in accordance with the present disclosure.
Figure 16:
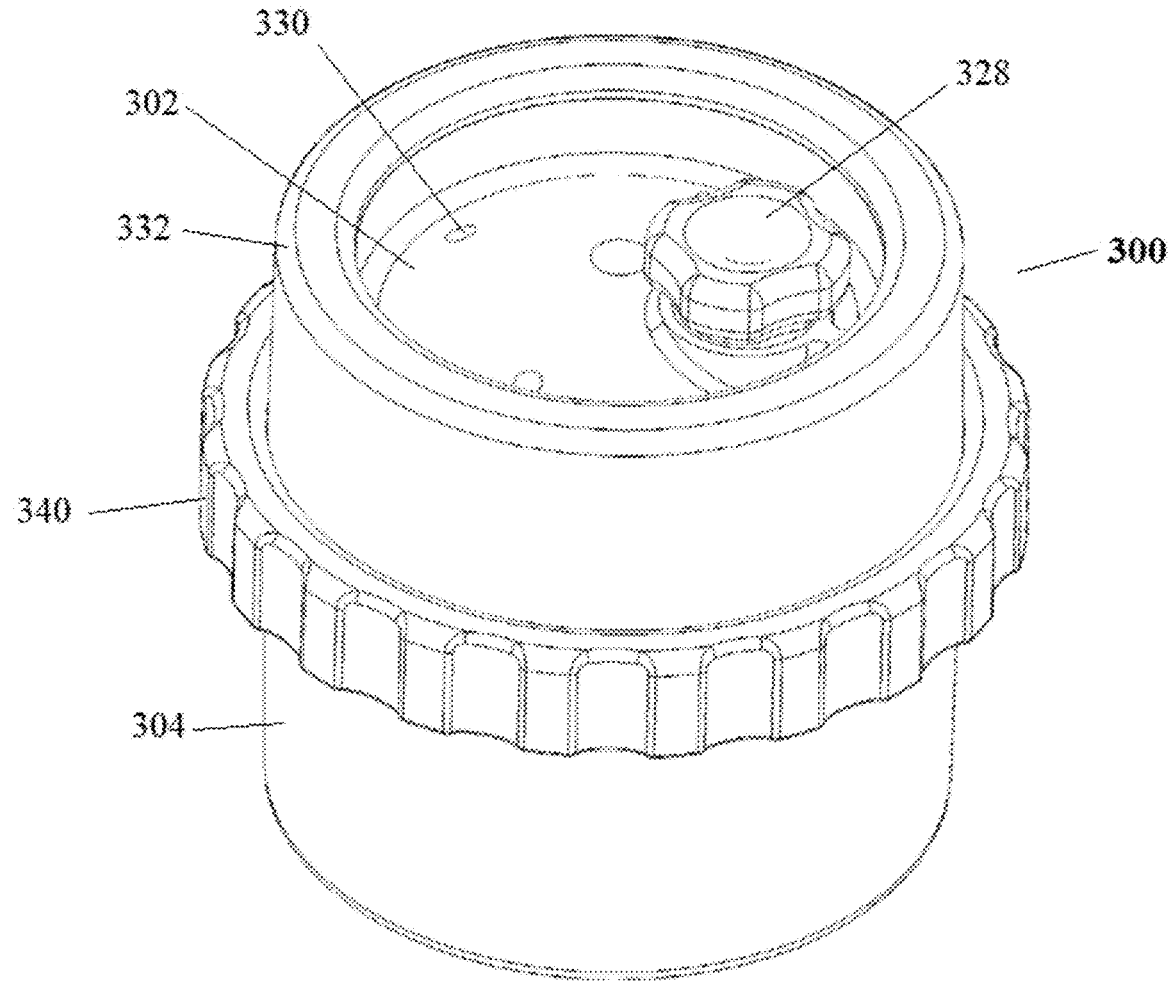
FIG. 16 is an illustration of an example of a hip head orthopedic mold constructed in accordance with the present disclosure.

The first and second housings 102, 104 may define one or more grooves, detents, lips, or other mating features complimentary to each other to aid in aligning and/or securing the components to one another, and to further resist separation when under pressure from injection of material into the mold and/or expansion or curing of an injected material. For example, as shown in FIG. 4, the first housing 12 may define a protrusion 118 on its lower end that is complementary and securely positionable within a groove or well 120 in the second housing 104. The first housing 102 may include or define a recessed groove 122 circumscribing or otherwise routing along the interior cavity 106, with the second housing 104 defining a complementary wall or protruding rib 124 circumscribing or otherwise routing around the interior cavity 106 that is securable in the groove 122. Providing such matable lock-and-key features provides increased resistance to separation between the housings, as well as reducing the likelihood of leakage at the coupling points between the first and second housings.

The first housing 102 may define an injection opening 126 in communication with the interior cavity 106 to allow the first and second housings 102, 104 to be filled with a curable material to form a prosthesis. An injection opening cap or cover 128 may also be included. The injection opening cap 128 may include a stamping component or indicia that imprints the injected molding material within the first and second cavities prior to curing. This allows the resulting prosthesis to have custom markings identifying the patient, infused pharmacological information, traceability information (lot number, manufacturing date, etc.), or the like. The injection cap 128 may further include a cutting surface or edge to remove, debride, or otherwise remove excess portions of the molded prosthesis once its cured. The first housing 102 may further define one or more vents 130 in an upper surface thereof to allow air pockets to escape, as well as provide an exit or spillway for excess material.

The first and second housings 102, 104 may be constructed from a polymer including one or more rubber or silicone components, and may have a durometer or hardness between Shore 40A and 80A. The first and second housings may provide a desired degree of pliability to facilitate removing a molded prosthesis from the interior cavities of the first and second housings.

The mold assembly 100 may include an exterior casing or shell that is releasably engageable to, and at least partially encompassing of, the first and second housings 102, 104 to secure the overall assembly and position of the first and second housings relative to one another during use. For example, the assembly 100 may include a first shell element 132 and a second shell element 134 that are releasably engageable to one another to at least partially enclose the first and second housings 102, 104 therein. The first shell element 132 may define an interior opening or cavity sized and shaped to receive at least a portion of the first housing 102 therein, and the second shell element 134 may define an interior opening or cavity sized and shaped to receive at least a portion of the second housing 104 therein. In the illustrated example, the first and second shell elements 132, 134 define substantially hollow cylindrical bodies positionable around substantially cylindrical exterior surfaces of the first and second housings 102, 104. Alternative variations in shapes and sizes may be implemented to accommodate varying prosthesis shapes.

The first and second shell elements may be constructed from a material having stronger and/or less pliable properties compared to that of the first and second housings to reduce or eliminate expansion, separation, and/or deformation of the first and second housings when the assembly 100 is used to manufacture a prosthesis. For example, the first and second shell elements may be constructed from one or more metals, polymers, or otherwise, and/or may have a durometer or hardness between Shore 40D and 80D.

The first and second housings 102, 104 may define one or more features facilitating alignment and/or prevention of rotation or unwanted displacement when secured inside of the first and second shell elements 132, 134. For example, each of the first and second housings may define one or more grooves 136a, 136b respectively, extending along or defined within an exterior surface of the housings. The grooves 136a, 136b may extend along the longitudinal length of the housings, and align with and receive a portion of respectively complementary protruding ribs 138a, 138b on interior surfaces of the first and second shell elements. When the first and second housings are positioned within the first and second shell elements, the aligned grooves 136a, 136b and ribs 138a, 138b restrict rotational movement of the housings with respect to the shell elements when the components of the assembly 100 are engaged and assembled to one another.

The femoral mold assembly 100 may include one or more connecting elements 140 to releasably secure the first shell element 132 to the second shell element 134. In the illustrated example, the connecting element 140 includes a threaded lock ring that engages threaded segments of both the first and second shell elements to secure the components together, thereby providing added rigidity and resistance to expansion or separation of the first and second shell elements, and thus the first and second housings contained therein when the assembly 100 is used to manufacture a prosthesis. Other examples of suitable connecting elements may include one or more clasps, fasteners, or other releasably engageable mechanisms.

Now turning to FIGS. 8-15, another example of an orthopedic prosthesis mold assembly 200 is shown that may be used to manufacture tibial-knee prostheses. The tibial mold assembly 200 may include features and characteristics similar to the mold assembly 100 and other features described herein. The mold assembly 200 generally includes a first housing or body 202 and a second housing or body 204 releasably engageable with the first housing. The first and second housings define cavities therein sized and shaped to produce an orthopedic prosthesis, such as that of a tibial knee joint component. For example, the first housing 202 may define or include a first cavity 206 therein for receiving a curable material to be formed or shaped into at least a portion of an orthopedic prosthesis. The second housing 204 may include a second cavity 208 for receiving a curable material to be formed or shaped into at least a portion of an orthopedic prosthesis. The second cavity 208 may be positional adjacent to and/or substantially congruous with the first cavity 206 when the first and second housings are engaged or coupled to one another to cooperatively from a substantially continuous prosthesis.

The mold assembly 200 may include a height-adjustable assembly of components that enables a physician to modify or select the resulting height of a prosthesis manufactured with the Assembly 200 to accommodate a range of varying anatomical dimensions of varying patients. For example, the assembly 200 may include a prosthesis mold insert 242 that is removably positionable within the cavity 208 of the second housing 204. The insert 242 may define one or more surface features configured to produce a resulting prosthesis with the desired contours and features for the particular anatomy at issue, in this example being a tibial knee component. The mold assembly 200 may also include one or more spacing elements 24 removably positionable within the cavity 208 of the second housing 204 that can be used to adjust the resulting depth or height of the cavity 208 that is filled with curable material. The spacing element(s) 244 may have a cross-sectional shape similar to that of the cavity 208, allowing multiple spacing element(s) 244 to be positioned into the cavity 108 underneath the mold insert 242 and thus adjust the open space in the cavity between the mold insert 242 and the top of the cavity 206 of the first housing. For example, to manufacture a prosthesis with a larger height, fewer spacing elements 244 would be inserted into the cavity 208, thereby allowing a larger mold space therein to be filled with curable molding material. As a result, a physician can select the quantity of spacing elements to insert into the cavity 208, thereby adjusting the relative height or distance of the mold space, and thus selecting and controlling the particular height of the molded prosthesis.

In an alternative to selecting a quantity of spacing elements to achieve the desired prosthesis height, a plurality of spacing elements 244 may be provided that each have a different height from the others, which allows a physician to select a single spacing element with the desired resulting height offset within the cavity 208. In another alternative example, a plurality of second housings 204 may be provided, with each of the plurality of second housings having a different depth or dimensioned cavity 208 compared to others of the plurality. In this example, a physician would select the housing 204 with the desired depth or height of the cavity 208 to create a prosthesis having the desired size.

The first and second housings 202, 204 may define one or more grooves, detents, lips, or other mating features complimentary to each other to aid in aligning and/or securing the components to one another, and to further resist separation when under pressure from injection of material into the mold and/or expansion or curing of an injected material. The second housing 204 may include or define a recessed groove 222 circumscribing or otherwise routing along the interior cavity 208, with the first housing 202 defining a complementary wall or protruding rib 224 circumscribing or otherwise routing around the interior cavity 206 that is securable in the groove 222. Providing such matable lock-and-key features provides increased resistance to separation between the housings, as well as reducing the likelihood of leakage at the coupling points between the first and second housings.

The first housing 202 may define an injection opening 226 in communication with the interior cavity 206 to allow the first and second housings 202, 204 to be filled with a curable material to form a prosthesis. An injection opening cap or cover 228 may also be included. The injection opening cap 228 may include a stamping component or indicia that imprints one or more indicia onto the injected molding material within the first and second cavities prior to curing. The injection cap 228 may further include a cutting surface or edge to remove, debride, or otherwise remove excess portions of the molded prosthesis once its cured. The first housing 202 may further define one or more vents 230 in an upper surface thereof to allow air pockets to escape, as well as provide an exit or spillway for excess material.

Similar to that of the assembly 100, the first and second housings 202, 204 of the assembly 200 may be constructed from a polymer including one or more rubber or silicone components, and may have a durometer or hardness between Shore 40A to 80A. The first and second housings may provide a desired degree of pliability to facilitate removing a molded prosthesis from the interior cavities of the first and second housings.

The mold assembly 200 may include an exterior casing or shell that is releasably engageable to, and at least partially encompassing of, the first and second housings 202, 204 to secure the overall assembly and position of the first and second housings relative to one another during use. For example, the assembly 200 may include a first shell element 232 and a second shell element 234 that are releasably engageable to one another to at least partially enclose the first and second housings 202, 204 therein. The first shell element 232 may define an interior opening or cavity sized and shaped to receive at least a portion of the first housing 202 therein, and the second shell element 234 may define an interior opening or cavity sized and shaped to receive at least a portion of the second housing 204 therein. In the illustrated example, the first and second shell elements 232, 234 define substantially hollow cylindrical bodies positionable around substantially cylindrical exterior surfaces of the first and second housings 202, 204. Alternative variations in shapes and sizes may be implemented to accommodate varying prosthesis shapes.

The first and second shell elements 232, 234 may be constructed from a material having stronger and/or less pliable properties compared to that of the first and second housings to reduce or eliminate expansion, separation, and/or deformation of the first and second housings when the assembly 200 is used to manufacture a prosthesis. For example, the first and second shell elements may be constructed from one or more metals, polymers, or otherwise, and/or may have a durometer or hardness between Shore 40D and 80D.

The first and second housings 202, 204 may define one or more features facilitating alignment and/or prevention of rotation or unwanted displacement when secured inside of the first and second shell elements 232, 234. For example, each of the first and second housings may define one or more grooves 236a, 236b respectively, extending along or defined within an exterior surface of the housings. The grooves 236a, 236b may extend along the longitudinal length of the housings, and align with and receive a portion of respectively complementary protruding ribs 238a, 238b on interior surfaces of the first and second shell elements. When the first and second housings are positioned within the first and second shell elements, the aligned grooves 236a, 236b and ribs 238a, 238b restrict rotational movement of the housings with respect to the shell elements when the components of the assembly 200 are engaged and assembled to one another.

The tibial mold assembly 200 may include one or more connecting elements 240 to releasably secure the first shell element 232 to the second shell element 234. In the illustrated example, the connecting element 240 includes a threaded lock ring that engages threaded segments of both the first and second shell elements to secure the components together, thereby providing added rigidity and resistance to expansion or separation of the first and second shell elements, and thus the first and second housings contained therein when the assembly 200 is used to manufacture a prosthesis. Other examples of suitable connecting elements may include one or more clasps, fasteners, or other releasably engageable mechanisms.

Now turning to FIGS. 16-21, another example of an orthopedic prosthesis mold assembly 300 is shown that may be used to manufacture hip head prostheses. The hip head mold assembly 300 may include features and characteristics similar to the mold assemblies 100, 200 and other features described herein. The mold assembly 300 generally includes a first housing or body 302 and a second housing or body 304 releasably engageable with the first housing. The first and second housings define cavities therein sized and shaped to produce an orthopedic prosthesis, such as that of a hip head joint component. For example, the first housing 302 may define or include a first cavity 306 therein for receiving a curable material to be formed or shaped into at least a portion of an orthopedic prosthesis. The second housing 304 may include a second cavity 308 for receiving a curable material to be formed or shaped into at least a portion of an orthopedic prosthesis. The second cavity 308 may be positional adjacent to and/or substantially congruous with the first cavity 306 when the first and second housings are engaged or coupled to one another to cooperatively from a substantially continuous prosthesis.

Figure 17A:
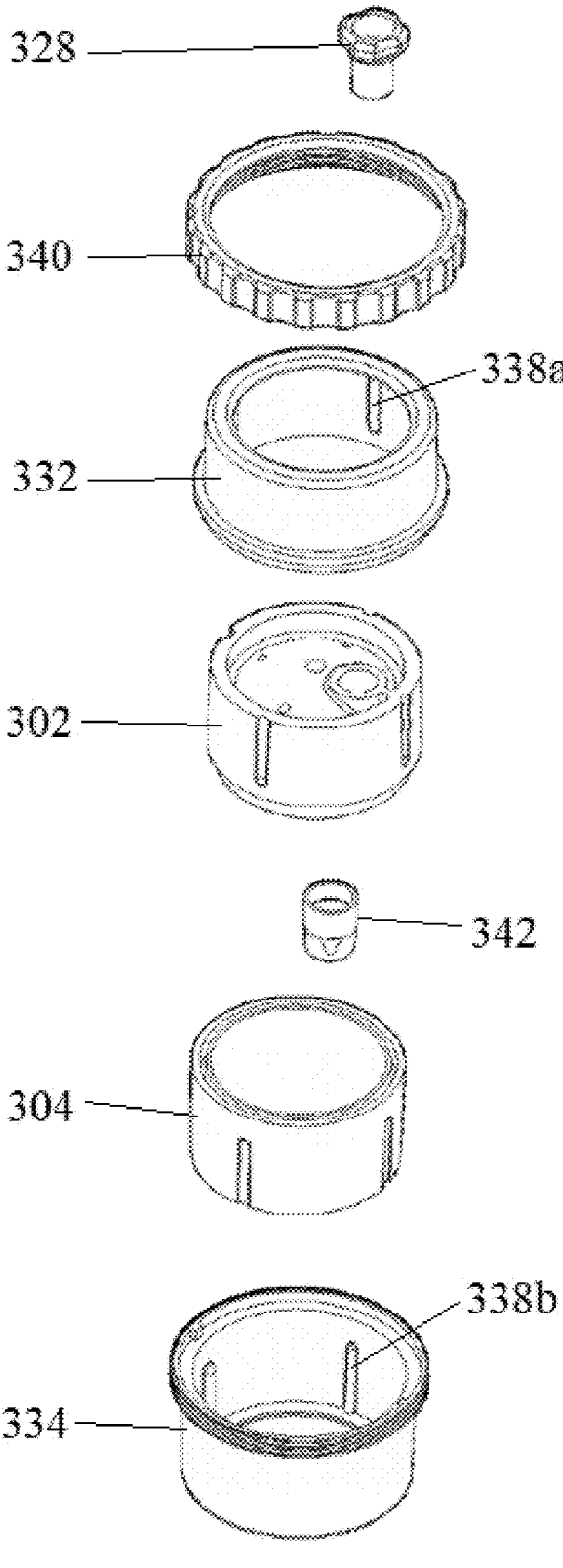
FIG. 17a is an exploded assembly illustration of the hip head orthopedic mold of FIG. 16.
Figure 17B:
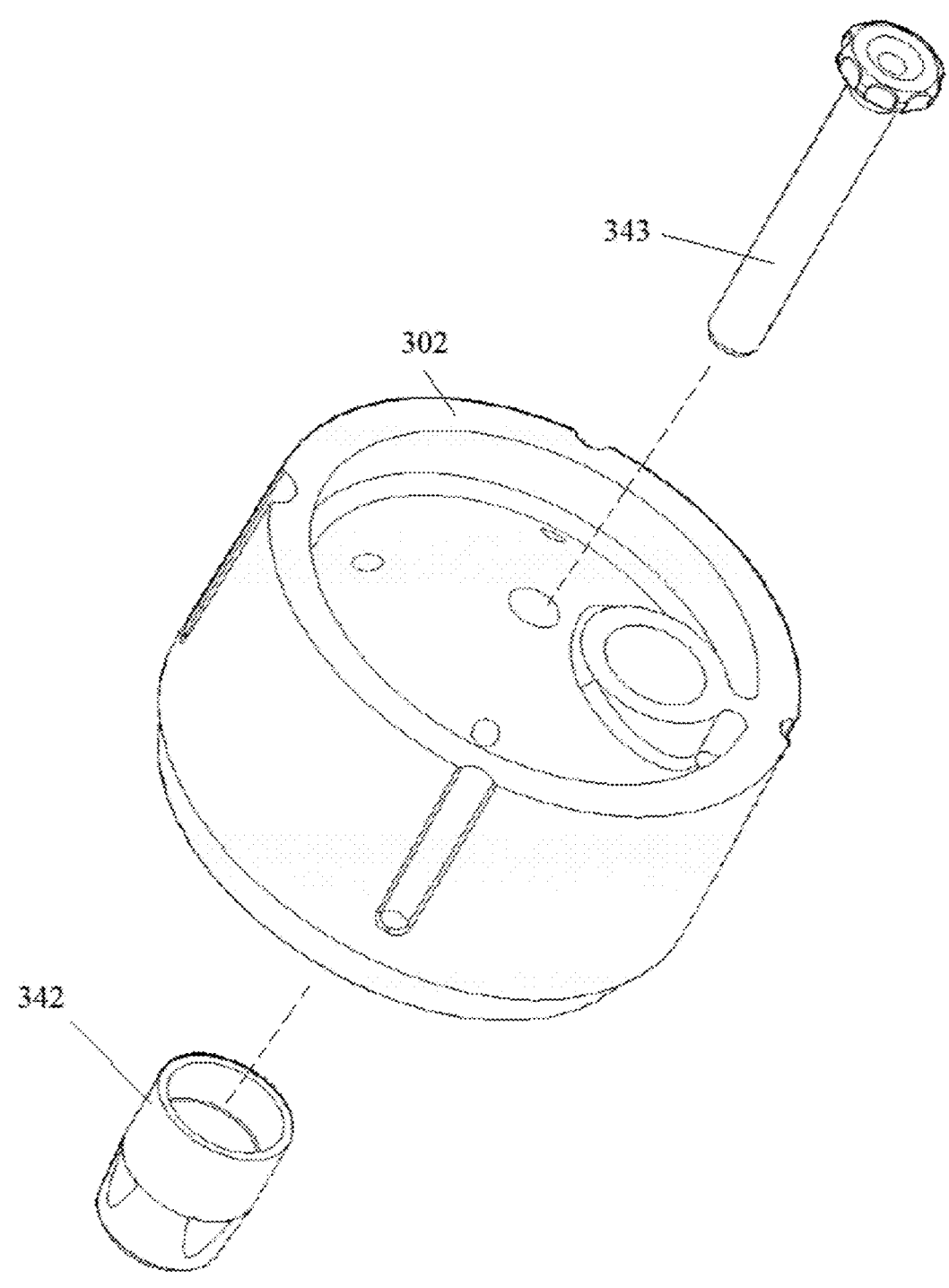
FIG. 17b is an exploded assembly illustration of another example of a hip head orthopedic mold.
Figure 18:
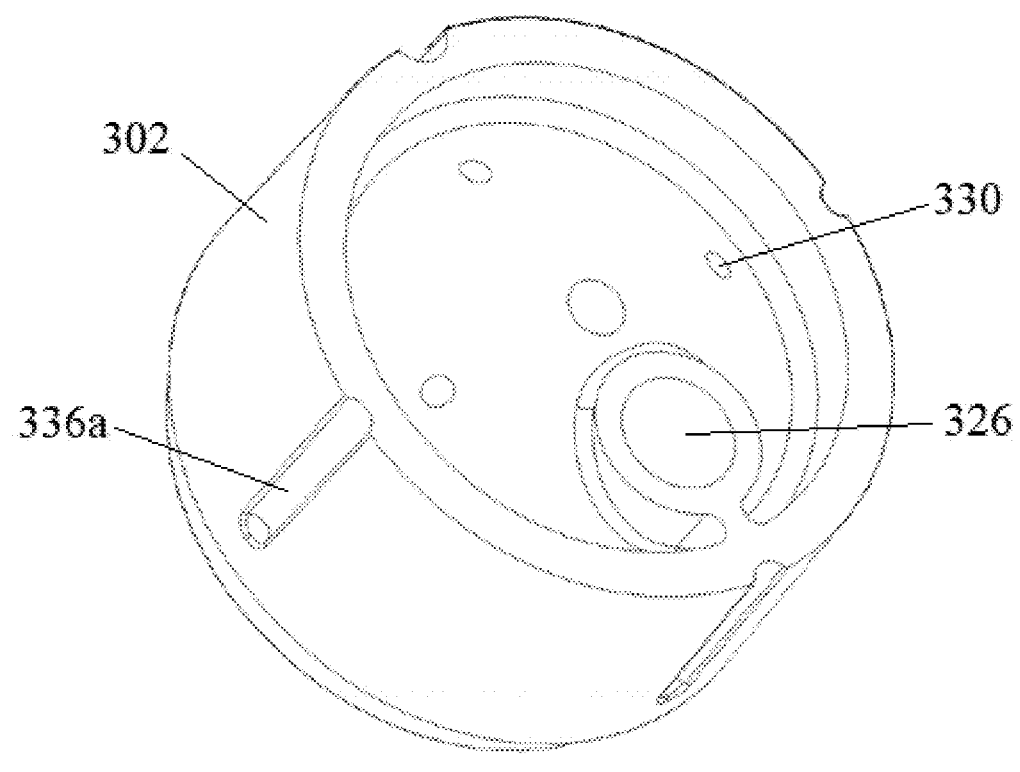
FIG. 18 is a top perspective view of an example of a first mold housing of the hip head orthopedic mold of FIG. 16.
Figure 19:
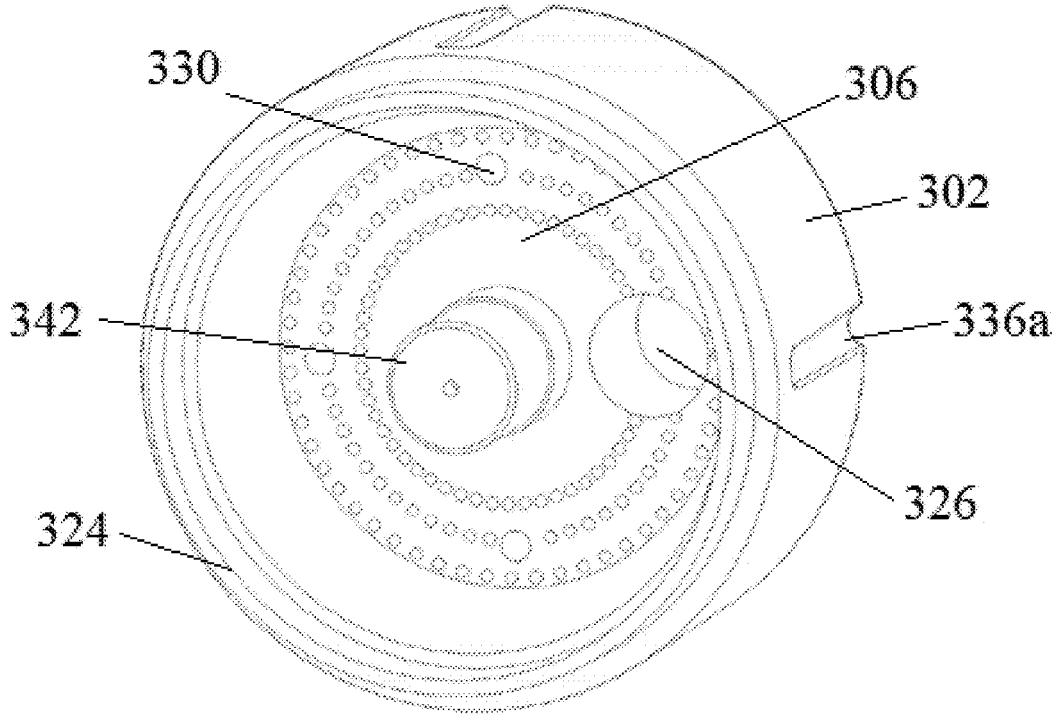
FIG. 19 is a bottom perspective view of the first mold housing of FIG. 18.
Figure 20:
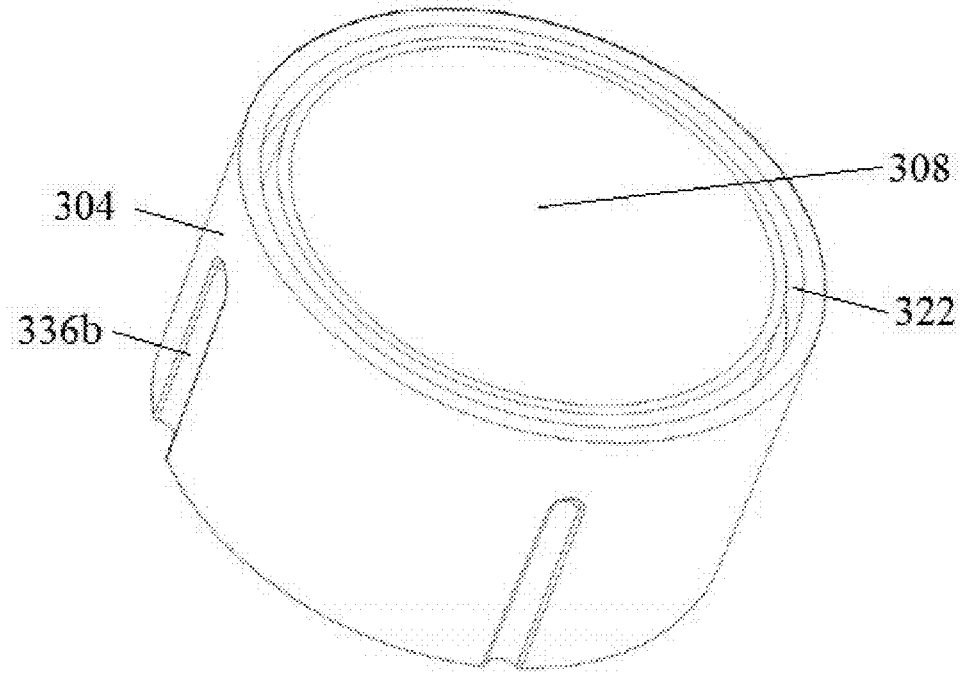
FIG. 20 is a top view of an example of a second mold housing of the hip head orthopedic mold of FIG. 61.
Figure 21:
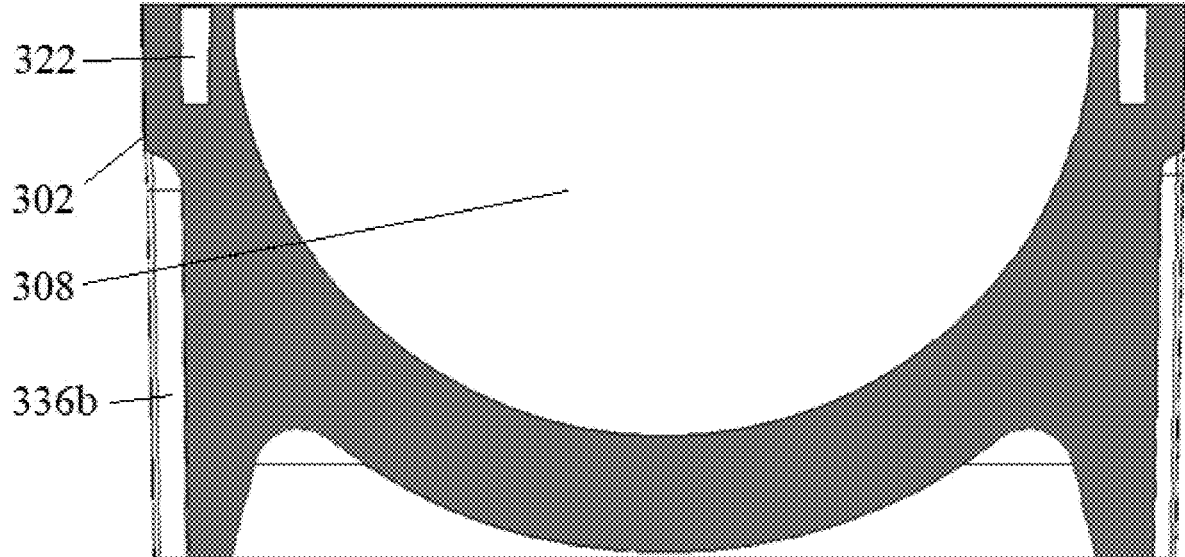
FIG. 21 is a cross-sectional view of the second mold housing of FIG. 20.
Figure 22:
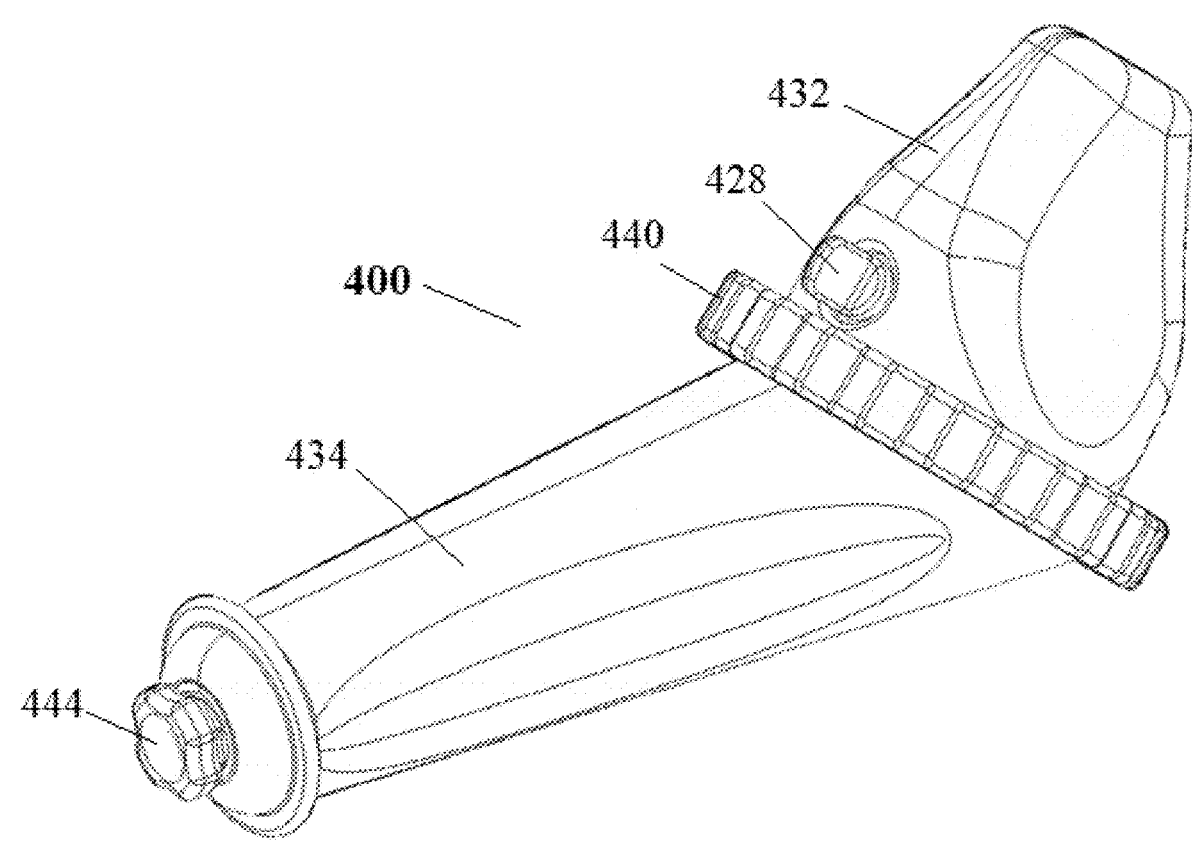
FIG. 22 is an illustration of an example of a hip stem orthopedic mold constructed in accordance with the present disclosure.

The mold assembly 300 may include a prosthesis insert 342 that is removably positionable within the cavity 306 of the first housing 302 that forms a part of the manufactured hip head prosthesis. For example, the insert 342 may include a socket or plug that is molded into the cured prosthesis to later receive a portion of a hip or femur stem implant component, such as the trunnion. As shown in FIG. 19, the insert 342 may releasably engage with a protrusion or other matable feature on an underside of the first housing 302 in a desired position with respect to the injected molding material and overall shape imparted by the mold assembly 300. In another example as shown in FIG. 17b, the insert 342 may engage with a pin 343 that is removably positionable through an opening in the first housing 302 to secure the insert in the desired position within the cavity 306. The attachment/engagement between the pin 343 and the insert 342 may be accomplished through a friction fit, temporary adhesive, or other releasable mechanisms.

The first and second housings 302, 304 may define one or more grooves, detents, lips, or other mating features complimentary to each other to aid in aligning and/or securing the components to one another, and to further resist separation when under pressure from injection of material into the mold and/or expansion or curing of an injected material. The second housing 304 may include or define a recessed groove 322 circumscribing or otherwise routing along the interior cavity 308, with the first housing 302 defining a complementary wall or protruding rib 324 circumscribing or otherwise routing around the interior cavity 306 that is securable in the groove 322. Providing such matable lock-and-key features provides increased resistance to separation between the housings, as well as reducing the likelihood of leakage at the coupling points between the first and second housings.

The first housing 302 may define an injection opening 326 in communication with the interior cavity 306 to allow the first and second housings 302, 304 to be filled with a curable material to form a prosthesis. An injection opening cap or cover 328 may also be included. The injection opening cap 328 may include a stamping component or indicia that imprints one or more indicia onto the injected molding material within the first and second cavities prior to curing. The injection cap 328 may further include a cutting surface or edge to remove, debride, or otherwise remove excess portions of the molded prosthesis once its cured. The first housing 302 may further define one or more vents 330 in an upper surface thereof to allow air pockets to escape, as well as provide an exit or spillway for excess material.

Similar to that of the assemblies described above, the first and second housings 302, 304 of the assembly 300 may be constructed from a polymer including one or more rubber or silicone components, and may have a durometer or hardness between Shore 40A and 80A. The first and second housings may provide a desired degree of pliability to facilitate removing a molded prosthesis from the interior cavities of the first and second housings.

The mold assembly 300 may include an exterior casing or shell that is releasably engageable to, and at least partially encompassing of, the first and second housings 302, 304 to secure the overall assembly and position of the first and second housings relative to one another during use. For example, the assembly 300 may include a first shell element 332 and a second shell element 334 that are releasably engageable to one another to at least partially enclose the first and second housings 302, 304 therein. The first shell element 332 may define an interior opening or cavity sized and shaped to receive at least a portion of the first housing 302 therein, and the second shell element 334 may define an interior opening or cavity sized and shaped to receive at least a portion of the second housing 304 therein. In the illustrated example, the first and second shell elements 332, 334 define substantially hollow cylindrical bodies positionable around substantially cylindrical exterior surfaces of the first and second housings 302, 304. Alternative variations in shapes and sizes may be implemented to accommodate varying prosthesis shapes.

The first and second shell elements 332, 334 may be constructed from a material having stronger and/or less pliable properties compared to that of the first and second housings to reduce or eliminate expansion, separation, and/or deformation of the first and second housings when the assembly 200 is used to manufacture a prosthesis. For example, the first and second shell elements may be constructed from one or more metals, polymers, or otherwise, and/or may have a durometer or hardness between Shore 40D and 80D.

The first and second housings 302, 304 may define one or more features facilitating alignment and/or prevention of rotation or unwanted displacement when secured inside of the first and second shell elements 332, 334. For example, each of the first and second housings may define one or more grooves 336a, 336b respectively, extending along or defined within an exterior surface of the housings. The grooves 336a, 336b may extend along the longitudinal length of the housings, and align with and receive a portion of respectively complementary protruding ribs 338a, 338b on interior surfaces of the first and second shell elements. When the first and second housings are positioned within the first and second shell elements, the aligned grooves 336a, 336b and ribs 338a, 338b restrict rotational movement of the housings with respect to the shell elements when the components of the assembly 300 are engaged and assembled to one another.

The mold assembly 300 may include one or more connecting elements 340 to releasably secure the first shell element 332 to the second shell element 334. In the illustrated example, the connecting element 340 includes a threaded lock ring that engages threaded segments of both the first and second shell elements to secure the components together, thereby providing added rigidity and resistance to expansion or separation of the first and second shell elements, and thus the first and second housings contained therein when the assembly 300 is used to manufacture a prosthesis. Other examples of suitable connecting elements may include one or more clasps, fasteners, or other releasably engageable mechanisms.

Now turning to FIGS. 22-25, another example of an orthopedic prosthesis mold assembly 400 is shown that may be used to manufacture hip or femoral stem prostheses. The hip stem mold assembly 400 may include features and characteristics similar to the mold assemblies 100, 200, 300 and other features described herein. The mold assembly 400 generally includes a first housing or body 402 and a second housing or body 404 releasably engageable with the first housing. The first and second housings define cavities therein sized and shaped to produce an orthopedic prosthesis, such as that of a hip head joint component. For example, the first housing 402 may define or include a first cavity 406 therein for receiving a curable material to be formed or shaped into at least a portion of an orthopedic prosthesis. The second housing 404 may include a second cavity 408 for receiving a curable material to be formed or shaped into at least a portion of an orthopedic prosthesis. The second cavity 408 may be positional adjacent to and/or substantially congruous with the first cavity 406 when the first and second housings are engaged or coupled to one another to cooperatively from a substantially continuous prosthesis.

Figure 23:
FIG. 23 is an exploded assembly illustration of the hip stem orthopedic mold of FIG. 22.
Figure 24:
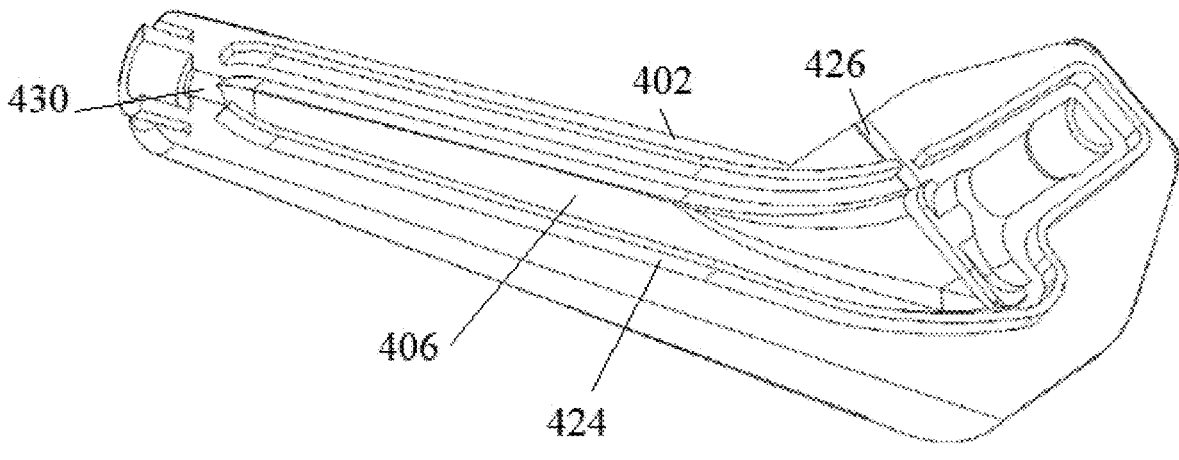
FIG. 24 is a perspective view of an example of a first mold housing of the hip stem orthopedic mold of FIG. 22.
Figure 25:
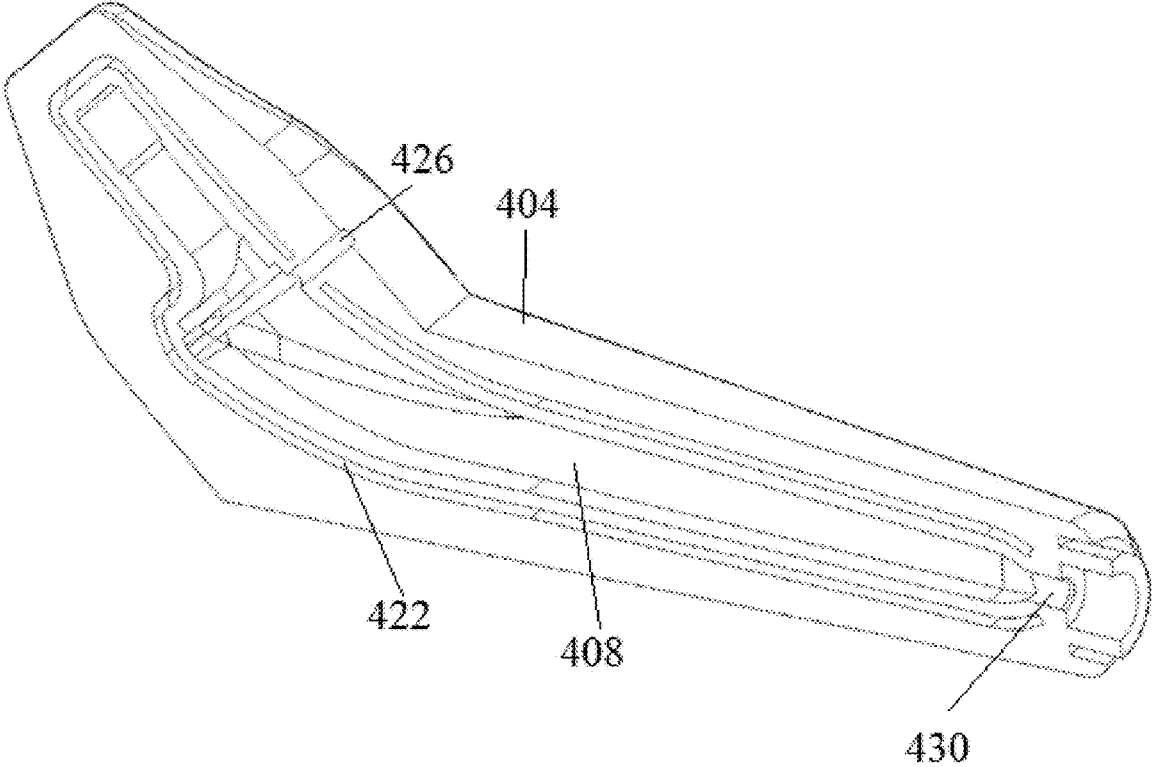
FIG. 25 is a perspective view of an example of a second mold housing of the hip stem orthopedic mold of FIG. 22.

The mold assembly 400 may include a prosthesis insert 442 that is removably positionable within the cavity 306 of the first housing 302 that forms a part of the manufactured hip stem prosthesis. For example, the insert 442 may include a metallic femur or hip stem that is at least partially encased within the molded, cured prosthesis, as shown in FIG. 23.

Figure 26:
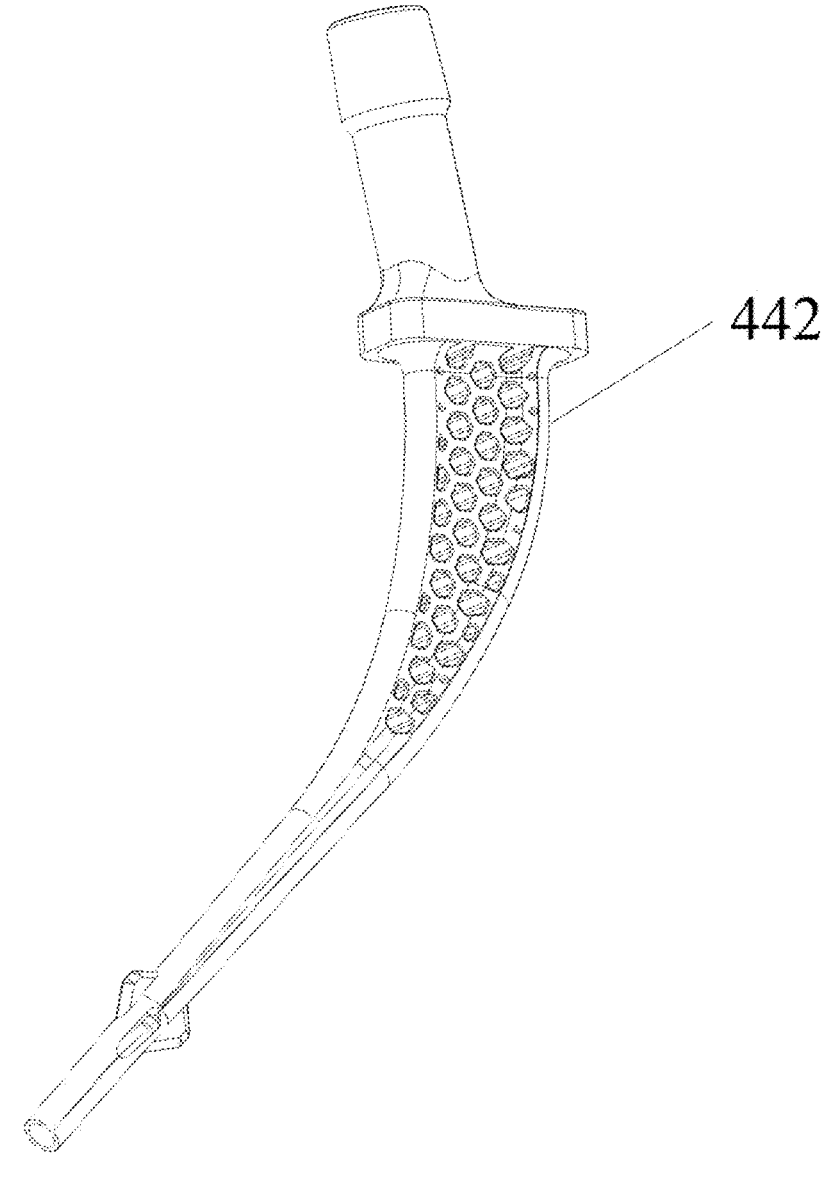
FIG. 26 is a perspective view of an example of a prosthesis insert for a hip stem orthopedic mold.

In another example as shown in FIG. 26, the insert 442 may define or include a porous lattice structure in the body of the stem insert to allow for the fenestration of PMMA and/or other mold materials in and around the insert 442. The porous structure may include one or more holes, cavities, honeycomb constructs, and/or other features machined, drilled, 3D printed, or otherwise implemented into a segment of the insert 442. This porous structure allows for numerous advantages, including but not limited to improved polymer, prosthesis, antibiotic, an/or biologic material attachment to the insert 442, which can mitigate delamination, fracture, or other failures of the prosthesis. Such lattice or honeycomb structure may be applied to different orthopedic inserts, such as those described herein for various arm, leg, knee or other joints.

The first and second housings 402, 404 may define one or more grooves, detents, lips, or other mating features complimentary to each other to aid in aligning and/or securing the components to one another, and to further resist separation when under pressure from injection of material into the mold and/or expansion or curing of an injected material.

The second housing 404 may include or define a recessed groove 422 circumscribing or otherwise routing along the interior cavity 408, with the first housing 402 defining a complementary wall or protruding rib 424 circumscribing or otherwise routing around the interior cavity 406 that is securable in the groove 422. Providing such matable lock-and-key features provides increased resistance to separation between the housings, as well as reducing the likelihood of leakage at the coupling points between the first and second housings.

The first housing 402 may define an injection opening 426 in communication with the interior cavity 406 to allow the first and second housings 402, 404 to be filled with a curable material to form a prosthesis. An injection opening cap or cover 428 may also be included. The injection opening cap 428 may include a stamping component or indicia that imprints one or more indicia onto the injected molding material within the first and second cavities prior to curing. The injection cap 428 may further include a cutting surface or edge to remove, debride, or otherwise remove excess portions of the molded prosthesis once its cured. The first housing 402 may further define one or more vents 430 in a surface thereof to allow air pockets to escape, as well as provide an exit or spillway for excess material. A vent plug or cap 444 may be included to removably cover the vent 430.

Similar to that of the assemblies described above, the first and second housings 402, 404 of the assembly 400 may be constructed from a polymer including one or more rubber or silicone components, and may have a durometer or hardness between Shore 40A and 80A. The first and second housings may provide a desired degree of pliability to facilitate removing a molded prosthesis from the interior cavities of the first and second housings.

The mold assembly 400 may include an exterior casing or shell that is releasably engageable to, and at least partially encompassing of, the first and second housings 402, 404 to secure the overall assembly and position of the first and second housings relative to one another during use. For example, the assembly 400 may include a first shell element 432 and a second shell element 434 that are releasably engageable to one another to at least partially enclose the first and second housings 402, 404 therein. The first shell element 432 may define an interior opening or cavity sized and shaped to receive at least a portion of the first housing 402 therein, and the second shell element 434 may define an interior opening or cavity sized and shaped to receive at least a portion of the second housing 404 therein.

The first and second shell elements 432, 434 may be constructed from a material having stronger and/or less pliable properties compared to that of the first and second housings to reduce or eliminate expansion, separation, and/or deformation of the first and second housings when the assembly 400 is used to manufacture a prosthesis. For example, the first and second shell elements may be constructed from one or more metals, polymers, or otherwise, and/or may have a durometer or hardness between Shore 40D and 80D.

The mold assembly 400 may include one or more connecting elements 440 to releasably secure the first shell element 432 to the second shell element 434. In the illustrated example, the connecting element 440 includes a threaded lock ring that engages threaded segments of both the first and second shell elements to secure the components together, thereby providing added rigidity and resistance to expansion or separation of the first and second shell elements, and thus the first and second housings contained therein when the assembly 400 is used to manufacture a prosthesis. Other examples of suitable connecting elements may include one or more clasps, fasteners, or other releasably engageable mechanisms.

For any of the assemblies disclosed herein, the first and seconds housings may be encased or reinforced by the exterior shell elements along differing axes or planes of attachment and alignment to further secure the assemblies together under the significant expansion pressures experienced by the mold when a curable material, such as PMMA or otherwise, is used to create a prosthesis. For example, as shown in FIG. 23, the first and second housings 402, 404 align and attach to each other (via the complementary wall and groove features, or as otherwise described herein) along a first axis 450. The first and second shell elements 432, 434 align and attach to each other along a second axis 452 that is not parallel to the first axis. The second axis may, for example, form an angle between 45 degrees and 135 degrees with the first axis. As a result, when the assembly 400 is assembled and curable molding material is injected into the inner cavities 406, 408 of the first and second housing 402, 404 respectively, the outward expansion pressure of the curable material will exert outward to attempt to separate the first and second housings 402, 404 where they join, i.e., generally along the axis 450. However, the first and second shell elements 423, 434 do not have a seam or joint along the axis 450 (instead joining and attaching along the second axis 452), and thus provide a uniform internal surface in the direction that the first and second housings 402, 404 join to one another. The expansion forces experienced within the cavities 406, 408 are thus directed uniformly throughout the cavities without separation of the first and second housings 402, 404 to provide a substantially uniform molded prosthesis.

Figure 27:
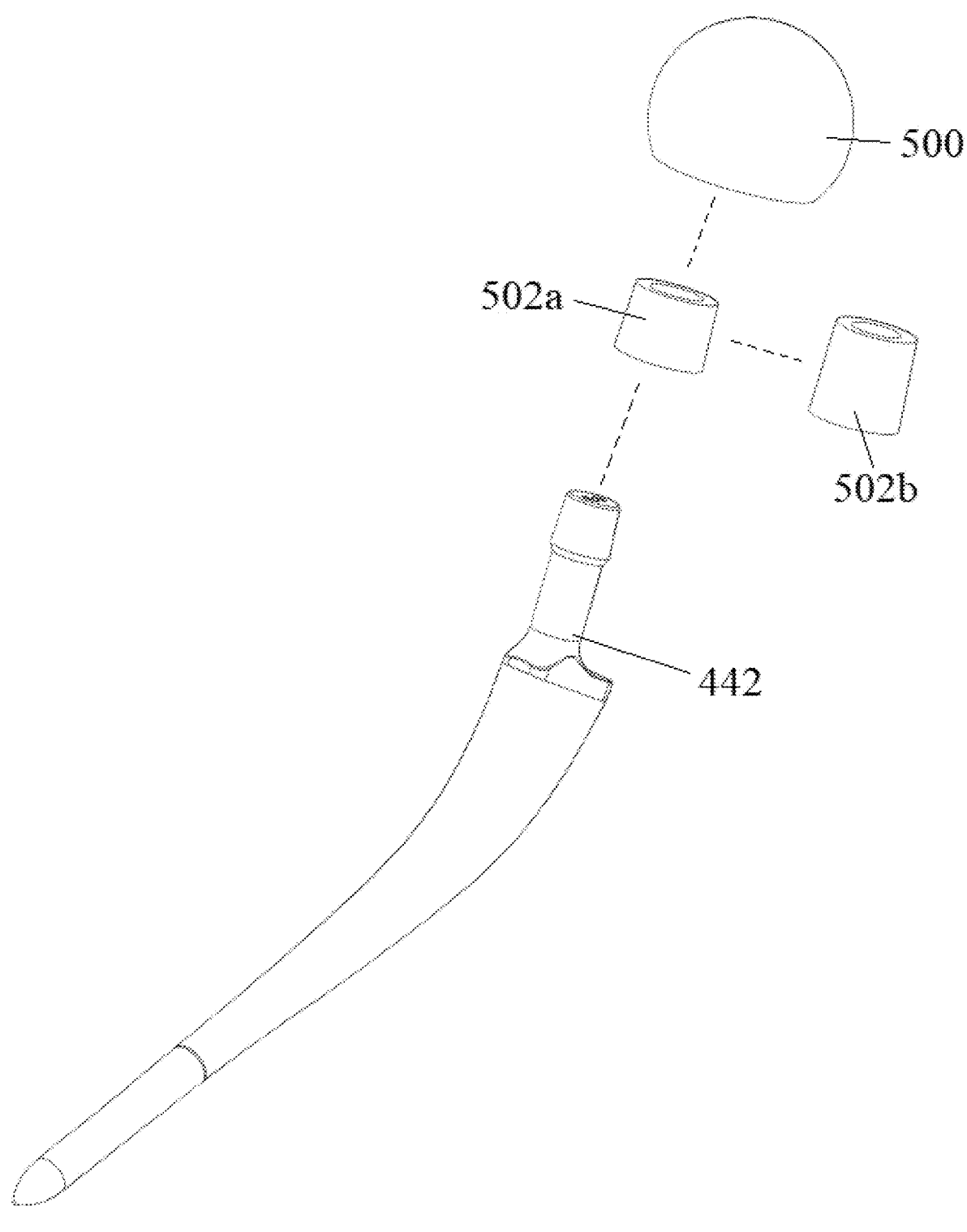
FIG. 27 is a perspective view of an example of a molded prosthesis kit constructed in accordance with the present disclosure.

The assemblies disclosed herein may include or otherwise be combined with additional components in a kit or system allowing a physician to modify, adjust, and/or otherwise conform a molded prosthesis to a specific patient. For example, as shown in FIG. 27, the molded stem insert 442 may be coupled to a molded hip head or acetabular cup 500 (which may be constructed using the molds and assemblies described herein). The relative height or position of the head 500 on the stem may be selectively adjustable by using one or more sleeves 502a, 502b, . . . (collectively referred to as '502') having varying heights. The physician may select the sleeve 502 having the height and dimensions providing the desired offset or positioning of the head 500 for the particular anatomy of a patient being addressed. Multiple sleeves having varying dimensions may be provided as a kit or system accompanying the mold assemblies described herein.

It will be appreciated by persons skilled in the art that the present disclosure is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the disclosure. A variety of modifications and variations are possible in light of the above teachings without departing from the scope and spirit of the disclosure, which is limited only by the following claims.

What is claimed is:

1. An orthopedic prosthesis mold system, comprising:
   a first housing including a first cavity therein shaped to form a portion of a tibial knee joint prosthesis;
   a second housing coupled to the first housing, the second housing including a second cavity therein shaped to form a portion of a tibial knee joint prosthesis;
   a plurality of spacing elements positionable within the second cavity of the second housing configured to selectively adjust a height of a prosthesis molded therein;
   a first shell element configured to receive at least a portion of the first housing therein;
   a second shell element configured to receive at least a portion of the first housing therein;
   a connection element releasably engageable to the first and second shell elements to prevent separation of the first shell element from the second shell element; and
   wherein the first and second housings are constructed from a material having a first hardness, and wherein the first and second shell elements are constructed from a material having a second hardness greater than the first hardness.

2. The orthopedic prosthesis mold system of claim 1, further comprising a mold insert positionable within the second cavity of the second housing, wherein the mold insert has a tibial condylar shape.

3. The orthopedic prosthesis mold system of claim 2, wherein the plurality of spacing elements are positionable within the second cavity of the second housing to adjust the location of the mold insert within the second cavity.

4. The orthopedic prosthesis mold system of claim 1, wherein the first and second housings are constructed from a material having a hardness between Shore 40A and 80A.

5. An orthopedic prosthesis mold system, comprising:
   a first housing including a first cavity therein shaped to form a portion of a tibial knee joint prosthesis;
   a second housing coupled to the first housing, the second housing including a second cavity therein shaped to form a portion of a tibial knee joint prosthesis;
   a plurality of spacing elements positionable within the second cavity of the second housing configured to selectively adjust a height of a prosthesis molded therein;
   a first shell element configured to receive at least a portion of the first housing therein;
   a second shell element configured to receive at least a portion of the first housing therein;
   a connection element releasably engageable to the first and second shell elements to prevent separation of the first shell element from the second shell element; and
   wherein the first and second shell elements are constructed from a material having a hardness between Shore 40D and 80D.

6. The orthopedic prosthesis mold system of claim 1, wherein the first and second housings align with and attach to one another along a first axis, and wherein the first and second shell elements align with and attach to one another along a second axis that is not parallel to the first axis.

7. The orthopedic prosthesis mold system of claim 1, wherein the first housing defines an injection port.

8. The orthopedic prosthesis mold system of claim 7, further comprising an injection port cap releasably engageable with the injection port to seal the injection port.

9. The orthopedic prosthesis mold system of claim 1, wherein the first and second shell elements are substantially cylindrical.

10. The orthopedic prosthesis mold system of claim 1, wherein the first housing defines a groove circumscribing the first cavity; and wherein the second housing defines a protruding wall circumscribing the second cavity, the wall being insertable into the groove.

11. The orthopedic prosthesis mold system of claim 1, wherein the first and second housings each define one or more longitudinal grooves in exterior surfaces thereof, wherein the first and second shell elements each define one or more protruding ribs on interior surfaces thereof, and wherein the protruding ribs are positionable in the longitudinal grooves.

12. An orthopedic prosthesis mold system, comprising:
a first housing including a first cavity therein shaped to form a portion of a hip stem prosthesis;
a second housing coupled to the first housing, the second housing including a second cavity therein shaped to form a portion of a hip stem prosthesis;
a first shell element configured to receive at least a portion of the first housing therein;
a second shell element configured to receive at least a portion of the first housing therein;
a connection element releasably engageable to the first and second shell elements to prevent separation of the first shell element from the second shell element; and wherein the first and second housings are constructed from a material having a first hardness, and wherein the first and second shell elements are constructed from a material having a second hardness greater than the first hardness.

13. The orthopedic prosthesis mold system of claim 12, further comprising a stem insert positionable within the second cavity of the second housing, wherein the stem insert defines a porous lattice structure in a portion thereof.

14. The orthopedic prosthesis mold system of claim 12, wherein the first and second housings align with and attach to one another along a first axis, and wherein the first and second shell elements align with and attach to one another along a second axis that is not parallel to the first axis.

15. The orthopedic prosthesis mold system of claim 12, wherein the first housing defines an injection port.

16. The orthopedic prosthesis mold system of claim 15, further comprising an injection port cap releasably engageable with the injection port to seal the injection port.

17. The orthopedic prosthesis mold system of claim 12, wherein the first housing defines a groove circumscribing the first cavity; and wherein the second housing defines a protruding wall circumscribing the second cavity, the wall being insertable into the groove.

18. The orthopedic prosthesis mold of claim 12, wherein the connection element includes a threaded lock ring engaging circumferentially threaded segments of the first and second shell elements.

* * * * *